US007332324B2

(12) United States Patent
Cole et al.

(10) Patent No.: US 7,332,324 B2
(45) Date of Patent: Feb. 19, 2008

(54) **ATTENUATED VACCINE USEFUL FOR IMMUNIZATIONS AGAINST *COCCIDIOIDES* SPP. INFECTIONS**

(75) Inventors: Garry T. Cole, San Antonio, TX (US); Xia Chen, Madison, WI (US); Kalpathi R. Seshan, Numgambakkan (IN); Chiung-Yu Hung, Helotes, TX (US); Jianmin Xue, San Antonio, TX (US); Jieh-Juen Yu, Helotes, TX (US)

(73) Assignee: University of Toledo, Toledo, OH (US)

( * ) Notice: Subject to any disclaimer, the term of this patent is extended or adjusted under 35 U.S.C. 154(b) by 0 days.

(21) Appl. No.: 11/292,431

(22) Filed: Dec. 2, 2005

(65) Prior Publication Data

US 2006/0121061 A1 Jun. 8, 2006

Related U.S. Application Data

(60) Provisional application No. 60/633,399, filed on Dec. 3, 2004.

(51) Int. Cl.
*A01N 63/04* (2006.01)

(52) U.S. Cl. .............................. 435/254.11; 424/274.1; 424/93.2; 424/93.5

(58) Field of Classification Search ..................... None
See application file for complete search history.

(56) References Cited

U.S. PATENT DOCUMENTS

| | | | |
|---|---|---|---|
| 4,877,611 | A | 10/1989 | Cantrell |
| 6,194,388 | B1 | 2/2001 | Krieg et al. |
| 6,207,646 | B1 | 3/2001 | Krieg et al. |
| 6,248,322 | B1 | 6/2001 | Klein et al. |
| 6,339,068 | B1 | 1/2002 | Krieg |

OTHER PUBLICATIONS

Chen et al. (Abstracts of the General Meeting of the American Society for Microbiology, May 2003).*

Reichard et al. (Infect. Immun., 68:5830-5838, 2000).*

Okeke et al. (Abstracts of the General Meeting of the American Society for Microbiology, May 2003).*

Bulawa, Christine E. et al. (Nov. 1995) "Attenuated virulence of chitin-deficient mutants of *Candida albicans," Proc. Natl. Acad. Sci. USA*, 92:10570-10574.

Cole, G.T. et al. (2001) "The parasitic cell wall of *Coccidioides immitis." Medical Mycology*, 39(Supplement 1):31-40.

Cole, G. T. et al. (Jun. 2004) "A vaccine against coccidioidomycosis is justified and attainable," *Medical Mycology*, 42:189-216.

Galgiani, John N. (Feb. 16, 1999) "Coccidioidomycosis: A Regional Disease of National Importance: Rethinking Approaches For Control." *Annals of Internal Medicine*, 130(4, Part I):293-300.

Galgiani, John N. (1993) "Coccidioidomycosis." *Western Journal of Medicine*, 159:153-171.

Georgopapadakou, Nafsika H. et al. (Mar. 1995) "The fungal cell wall as a drug target," *Trends in Microbiology*, 3(3):98-104.

Kuranda, Michael J. et al. (Oct. 15, 1991) "Chitinase Is Required For Cell Separation During Growth Of *Saccharomyces cerevisiae." Journal of Biological Chemistry*, 266(29):19758-19767.

Levine, H. B. et al. (1961) "Immunogenicity of Spherule-Endospore Vaccines of *Coccidioides immitis* for Mice," *Journal of Immunology*, 87: 218-227.

Levine, H. B. et al. (1965) "Immunization of Mice to *Coccidioides immitis*: Dose, Regimen and Spherulation Stage of Killed Spherule Vaccines," *Journal of Immunology*, 94(1):132-142.

Liu, H. et al. (2001) "Relevance of chitin and chitin synthases to virulence in *Wangiella* (*Exophiala*) *dermatitidis*, a model of melanized pathogen of humans." *Chitin Enzymology 2001*, R.A.A. Muzzarelli (ed.), Atec Edizioni, Italy, pp. 463-472.

Mattern, I.E. et al. (1988) "A vector for *Aspergillus* transformation conferring phleomycin resistance." *Medical Biological Laboratory TNO*, The Netherlands, 1 page.

O'Hagan, Derek T. et al. (2001) "Recent developments in adjuvants for vaccines against infectious diseases." *Biomolecular Engineering*, 18(3):69-85.

Pappagianis, D. et al. (1961) "Immunization of mice with viable *Coccidioides immitis." Journal of Immunology*, 86:28-34.

Pappagianis, Demosthenes et al. (1993) "Evaluation of the Protective Efficacy of the Killed *Coccidioides immitis* Spherule Vaccine in Humans." *American Review of Respiratory Diseases*, 148:656-660.

Punt, Peter J. et al. (1987) "Transformation of *Aspergillus* based on the hygromycin B resistance marker from *Escherichia coli." Gene*, 56:117-124.

Ronaghy, A. et al. (2002) "Immunostimulatory DNA Sequences Influence the Course of Adjuvant Arthritis." *J. Immunol.*, 168(1):51-56.

Takaya, Naoki et al. (1998) "Cloning and Characterization of a Chitinase-encoding Gene (*chiA*) from *Aspergillus nidulans*, Disruption of Which Decreases Germination Frequency and Hyphal Growth." *Bioscience, Biotechnology, and Biochemistry*, 62(1):60-65.

Walch, Henry A., Jr. et al. (1960) "Studies with Induced Mutants of *Coccidioides immitis." Proceedings of the Second Symposium on Coccidioidomycosis*, L. Ajello (ed.), University of Arizona Press, p. 339-347.

Walch, H.A. et al. (1971) "Immunization of mice with induced mutants of *Coccidioides immitis*. I. Characterization of mutants and preliminary studies of their use as viable vaccines." *Sabouraudia*, 9:173-184.

* cited by examiner

*Primary Examiner*—Robert A. Zeman
*Assistant Examiner*—Brian Gangle
(74) *Attorney, Agent, or Firm*—Morrison & Foerster LLP

(57) ABSTRACT

A Coccidioides spp. fungus that is attenuated by the loss of endosporulation potential of the fungus wherein said fungus does not replicate when transformed into the parasitic phase.

7 Claims, No Drawings

SEQUENCE LISTING

```
<160> NUMBER OF SEQ ID NOS: 37

<210> SEQ ID NO 1
<211> LENGTH: 3090
<212> TYPE: DNA
<213> ORGANISM: Coccidioides posadasii
```

-continued

<400> SEQUENCE: 1

```
ccgtcgaggg agtctgatag cccttgttta gtatgggtct ctctggcttg agcctcataa     60
tctcttcgtc ttcctgtccc tccttaaatc ttttttatag agtgatatct ccatttcctc    120
tccttgtcca tctgcattgc agcagccata ccctgcaaac ctctggtttg cgtcctttcc    180
ttgagtgcac taccagcctc acgtcctgtt gggccggctt gcttaccctc gtttgcctgg    240
agattacttt ggcccatcta ccatcctttt aatcatgggg ccaactaata ttcttgcagc    300
gtttatcgct gtgtcctctc tttttatcca gtcactcgct ctcaatccct acgccaaaag    360
taatttggca gtctactggg tatgagccaa ttactttagc gcccttggtt gtcttgatgc    420
tcacctttct ggttgattag gggcaaggag ctgggcagaa ccggctcagc tacttctgcg    480
aaaagaccag ctttgatatc attgttgtgg gtttcatcaa tgtgttcccc gaccaaggcc    540
ccgccggatg gccgggcagc aattttggaa accaatgcgc cgattcgtat tactatacaa    600
aaaatgggac gaagaccaag cttttggatg gctgttatca gattaaggaa gatcttccca    660
agtgcaaggc gctggggaag acgatcctgc tctccctagg cggaggagcc gtgcacgatt    720
tctacgaggt caagagcgaa gagtccgctc ttaattttgc ggatttcctt tggggcgcat    780
tcggcccact gacaccagac tggactggac ctcgtccatt cggagaggcc tcagtcgatg    840
gatttgactt cgatatcgaa aagggtagta actttggtat gtatcccgtt ctcccttcca    900
ggtgattcga gtccctgact gacgaaagta ggctattcaa ttatggtccg acgtttgcga    960
gaacttttcc tccaggaccc gctcaacaga tactatatct ctgcagcccc ccagtgcata   1020
atgccagata agtatctctc acatgcgata tctaattcgg cgttcgactt catcttcatc   1080
cagttctaca acaatccttc gtgctctgcc aaacggtggg tgactaaccc caagtccgtg   1140
acgtacaccg tggacgattg ggtcaaatac atccgcaaaa gcggaaaccc attagcgaaa   1200
cttttcattg gccttcccgc atctaagtct gctgctgcga aagaagacta tcttactcct   1260
ggtgaagcca ccaaaatcgt cagcacgtac atggcgaaat atccaagtac ttttggtggt   1320
atgatggtgt gggaagcaac tgcatcggag aacaataagc ttggcggact tccatacgcc   1380
gatataatga aggaagtgct gttgcgatgc gatccggatc cccctaccag tactgttaca   1440
agtaccacat ctgcctcgac ttcaacccag acttcatctc aaagcactac tatggaaacc   1500
aagactttgt cggcttctac gaccccgagc agtccgagta ctgtgtcgcc aagttcaaca   1560
atgcagacaa cctctactgg ttcaacttcc attgagactg tcacaacgag aagtcaagag   1620
ccaccatcaa caacaatctc cacaaggtca gcttccactg agcctgtaac aacgagaagt   1680
caagagccac catcaaccac aatctccaca aggtcagctt ccactgagac tgtgacgaca   1740
agaagtcaag agccaccatc aaccacaatc tccacatggt cggcctccac tgaaactagt   1800
acaagcagcc aggattcacc atccacgaca atttcgacga agtctgcgcc cactggcact   1860
gtcacaacta ggagtcagga tttaccctca acgaccatct ctacgagatc tcctgagact   1920
gaaactgaga ctgcaacaac aaaaagtcag ggttcaccgt caattactct ctctacaagg   1980
tcttcctccg ctgagactgt atcaacaaga agtcagcatt catcgtctac aacaatttca   2040
acgaagtctg caccaactga gactggtacg acaagtgaac attcaacatc aatgcctgtc   2100
tctacgagat cggcttccac cgagactgta ataacgagaa gtcagaattc agattctcaa   2160
tcaatgacag tctctacaag atcgccttcc accgaaagta tcacaacaag aagtcaaggt   2220
tcgccatcag agacattttc aaccaagtct gttccagtag ataccatctc aactgaattg   2280
ccttctcaaa cgccaacaac gattataacg ggaacacctt ctgatcctgt atcagccccg   2340
```

-continued accaccacgg ttcctcccaa tcctaccctg acgctcgccc catcttcctc cacaacagaa 2400
gaccgcacca caatcactac tataatcacc acatcctacg tcactgtctg tcccactggc 2460
tttaccacgg tcacaataac atacaccacc acctactgcc cggagaccgc ttcgctcacg 2520
ccaactcagc cccctattcc gggagctcca gcccctccac cagatggctg gacaacaatt 2580
gtcaccgtgt gcccccagtg cgccccaacg ccaactaccg tcacactcac ggtccccaca 2640
agatctgcct tccttcccgc acgcacggag actcgccctg ttgtcactgt ggtcccagtg 2700
ccggagaatc caattaagaa cgtgaagcct agtgagtccg gagattttgt gactgttact 2760
acagcggcgc cggcaacggt tacaaagacg ttggaataca acaacccggt ggattccgat 2820
gtgaatgtcc aacccacggg tggtagttcc cccgtcgagt ttgaaggcag tgcgatgact 2880
gtaagaagta tggatgtggt cgcgaaagcc ctgattaccg ctggagcgct gtgttgggat 2940
tgttcttggg gttataatct gttaatttgc tgaggcgata tatacacatt ttcttcggag 3000
gggtgtgtac ataatgtcac gggtgctgta cttgtacata cttgacactt acctacatat 3060
acagtacata tatacttcat atccctcgag 3090

<210> SEQ ID NO 2
<211> LENGTH: 2583
<212> TYPE: DNA
<213> ORGANISM: Coccidioides posadasii

<400> SEQUENCE: 2
atggggccaa ctaatattct tgcagcgttt atcgctgtgt cctctctttt tatccagtca 60
ctcgctctca atccctacgc caaaagtaat ttggcagtct actgggggca aggagctggg 120
cagaaccggc tcagctactt ctgcgaaaag accagctttg atatcattgt tgtgggtttc 180
atcaatgtgt tccccgacca aggccccgcc ggatggccgg gcagcaattt tggaaaccaa 240
tgcgccgatt cgtattacta tacaaaaaat gggacgaaga ccaagctttt ggatggctgt 300
tatcagatta aggaagatct tcccaagtgc aaggcgctgg ggaagacgat cctgctctcc 360
ctaggcggag gagccgtgca cgatttctac gaggtcaaga gcgaagagtc cgctcttaat 420
tttgcggatt tcctttgggg cgcattcggc ccactgacac cagactggac tggacctcgt 480
ccattcggag aggcctcagt cgatggattt gacttcgata tcgaaaaggg tagtaacttt 540
ggctattcaa ttatggtccg acgtttgcga gaacttttcc tccaggaccc gctcaacaga 600
tactatatct ctgcagcccc ccagtgcata atgccagata agtatctctc acatgcgata 660
tctaattcgg cgttcgactt catcttcatc cagttctaca acaatccttc gtgctctgcc 720
aaacggtggg tgactaaccc caagtccgtg acgtacaccg tggacgattg ggtcaaatac 780
atccgcaaaa gcggaaaccc attagcgaaa cttttcattg gccttcccgc atctaagtct 840
gctgctgcga aagaagacta tcttactcct ggtgaagcca ccaaaatcgt cagcacgtac 900
atggcgaaat atccaagtac ttttggtggt atgatggtgt gggaagcaac tgcatcggag 960
aacaataagc ttggcggact tccatacgcc gatataatga aggaagtgct gttgcgatgc 1020
gatccggatc cccctaccag tactgttaca agtaccacat ctgcctcgac ttcaacccag 1080
acttcatctc aaagcactac tatggaaacc aagactttgt cggcttctac gaccccgagc 1140
agtccgagta ctgtgtcgcc aagttcaaca atgcagacaa cctctactgg ttcaacttcc 1200
attgagactg tcacaacgag aagtcaagag ccaccatcaa caacaatctc cacaaggtca 1260
gcttccactg agcctgtaac aacgagaagt caagagccac catcaaccac aatctccaca 1320

-continued

```
aggtcagctt ccactgagac tgtgacgaca agaagtcaag agccaccatc aaccacaatc   1380

tccacatggt cggcctccac tgaaactagt acaagcagcc aggattcacc atccacgaca   1440

atttcgacga agtctgcgcc cactggcact gtcacaacta ggagtcagga tttaccctca   1500

acgaccatct ctacgagatc tcctgagact gaaactgaga ctgcaacaac aaaaagtcag   1560

ggttcaccgt caattactct ctctacaagg tcttcctccg ctgagactgt atcaacaaga   1620

agtcagcatt catcgtctac aacaatttca acgaagtctg caccaactga gactggtacg   1680

acaagtgaac attcaacatc aatgcctgtc tctacgagat cggcttccac cgagactgta   1740

ataacgagaa gtcagaattc agattctcaa tcaatgacag tctctacaag atcgccttcc   1800

accgaaagta tcacaacaag aagtcaaggt tcgccatcag agacattttc aaccaagtct   1860

gttccagtag ataccatctc aactgaattg ccttctcaaa cgccaacaac gattataacg   1920

ggaacacctt ctgatcctgt atcagccccg accaccacgg ttcctcccaa tcctaccctg   1980

acgctcgccc catcttcctc cacaacagaa gaccgcacca caatcactac tataatcacc   2040

acatcctacg tcactgtctg tcccactggc tttaccacgg tcacaataac atacaccacc   2100

acctactgcc cggagaccgc ttcgctcacg ccaactcagc cccctattcc gggagctcca   2160

gcccctccac cagatggctg gacaacaatt gtcaccgtgt gcccccagtg cgccccaacg   2220

ccaactaccg tcacactcac ggtccccaca agatctgcct tccttcccgc acgcacggag   2280

actcgccctg ttgtcactgt ggtcccagtg ccggagaatc caattaagaa cgtgaagcct   2340

agtgagtccg gagattttgt gactgttact acagcggcgc cggcaacggt tacaaagacg   2400

ttggaataca acaacccggt ggattccgat gtgaatgtcc aacccacggg tggtagttcc   2460

cccgtcgagt ttgaaggcag tgcgatgact gtaagaagta tggatgtggt cgcgaaagcc   2520

ctgattaccg ctggagcgct gtgttgggat tgttcttggg gttataatct gttaatttgc   2580

tga                                                                 2583
```

```
<210> SEQ ID NO 3
<211> LENGTH: 860
<212> TYPE: PRT
<213> ORGANISM: Coccidioides posadasii

<400> SEQUENCE: 3

Met Gly Pro Thr Asn Ile Leu Ala Ala Phe Ile Ala Val Ser Ser Leu
 1               5                  10                  15

Phe Ile Gln Ser Leu Ala Leu Asn Pro Tyr Ala Lys Ser Asn Leu Ala
            20                  25                  30

Val Tyr Trp Gly Gln Gly Ala Gly Gln Asn Arg Leu Ser Tyr Phe Cys
        35                  40                  45

Glu Lys Thr Ser Phe Asp Ile Ile Val Val Gly Phe Ile Asn Val Phe
    50                  55                  60

Pro Asp Gln Gly Pro Ala Gly Trp Pro Gly Ser Asn Phe Gly Asn Gln
65                  70                  75                  80

Cys Ala Asp Ser Tyr Tyr Tyr Thr Lys Asn Gly Thr Lys Thr Lys Leu
                85                  90                  95

Leu Asp Gly Cys Tyr Gln Ile Lys Glu Asp Leu Pro Lys Cys Lys Ala
            100                 105                 110

Leu Gly Lys Thr Ile Leu Leu Ser Leu Gly Gly Gly Ala Val His Asp
        115                 120                 125

Phe Tyr Glu Val Lys Ser Glu Glu Ser Ala Leu Asn Phe Ala Asp Phe
    130                 135                 140
```

-continued

```
Leu Trp Gly Ala Phe Gly Pro Leu Thr Pro Asp Trp Thr Gly Pro Arg
145                 150                 155                 160

Pro Phe Gly Glu Ala Ser Val Asp Gly Phe Asp Phe Asp Ile Glu Lys
                165                 170                 175

Gly Ser Asn Phe Gly Tyr Ser Ile Met Val Arg Arg Leu Arg Glu Leu
            180                 185                 190

Phe Leu Gln Asp Pro Leu Asn Arg Tyr Tyr Ile Ser Ala Ala Pro Gln
        195                 200                 205

Cys Ile Met Pro Asp Lys Tyr Leu Ser His Ala Ile Ser Asn Ser Ala
    210                 215                 220

Phe Asp Phe Ile Phe Ile Gln Phe Tyr Asn Asn Pro Ser Cys Ser Ala
225                 230                 235                 240

Lys Arg Trp Val Thr Asn Pro Lys Ser Val Thr Tyr Thr Val Asp Asp
                245                 250                 255

Trp Val Lys Tyr Ile Arg Lys Ser Gly Asn Pro Leu Ala Lys Leu Phe
            260                 265                 270

Ile Gly Leu Pro Ala Ser Lys Ser Ala Ala Ala Lys Glu Asp Tyr Leu
        275                 280                 285

Thr Pro Gly Glu Ala Thr Lys Ile Val Ser Thr Tyr Met Ala Lys Tyr
    290                 295                 300

Pro Ser Thr Phe Gly Gly Met Met Val Trp Glu Ala Thr Ala Ser Glu
305                 310                 315                 320

Asn Asn Lys Leu Gly Gly Leu Pro Tyr Ala Asp Ile Met Lys Glu Val
                325                 330                 335

Leu Leu Arg Cys Asp Pro Asp Pro Pro Thr Ser Thr Val Thr Ser Thr
            340                 345                 350

Thr Ser Ala Ser Thr Ser Thr Gln Thr Ser Ser Gln Ser Thr Thr Met
        355                 360                 365

Glu Thr Lys Thr Leu Ser Ala Ser Thr Thr Pro Ser Ser Pro Ser Thr
    370                 375                 380

Val Ser Pro Ser Ser Thr Met Gln Thr Thr Ser Thr Gly Ser Thr Ser
385                 390                 395                 400

Ile Glu Thr Val Thr Thr Arg Ser Gln Glu Pro Pro Ser Thr Thr Ile
                405                 410                 415

Ser Thr Arg Ser Ala Ser Thr Glu Pro Val Thr Thr Arg Ser Gln Glu
            420                 425                 430

Pro Pro Ser Thr Thr Ile Ser Thr Arg Ser Ala Ser Thr Glu Thr Val
        435                 440                 445

Thr Thr Arg Ser Gln Glu Pro Pro Ser Thr Thr Ile Ser Thr Trp Ser
    450                 455                 460

Ala Ser Thr Glu Thr Ser Thr Ser Ser Gln Asp Ser Pro Ser Thr Thr
465                 470                 475                 480

Ile Ser Thr Lys Ser Ala Pro Thr Gly Thr Val Thr Thr Arg Ser Gln
                485                 490                 495

Asp Leu Pro Ser Thr Thr Ile Ser Thr Arg Ser Pro Glu Thr Glu Thr
            500                 505                 510

Glu Thr Ala Thr Thr Lys Ser Gln Gly Ser Pro Ser Ile Thr Leu Ser
        515                 520                 525

Thr Arg Ser Ser Ser Ala Glu Thr Val Ser Thr Arg Ser Gln His Ser
    530                 535                 540

Ser Ser Thr Thr Ile Ser Thr Lys Ser Ala Pro Thr Glu Thr Gly Thr
545                 550                 555                 560

Thr Ser Glu His Ser Thr Ser Met Pro Val Ser Thr Arg Ser Ala Ser
```

-continued

```
                565                 570                 575

Thr Glu Thr Val Ile Thr Arg Ser Gln Asn Ser Asp Ser Gln Ser Met
            580                 585                 590

Thr Val Ser Thr Arg Ser Pro Ser Thr Glu Ser Ile Thr Thr Arg Ser
        595                 600                 605

Gln Gly Ser Pro Ser Glu Thr Phe Ser Thr Lys Ser Val Pro Val Asp
    610                 615                 620

Thr Ile Ser Thr Glu Leu Pro Ser Gln Thr Pro Thr Thr Ile Ile Thr
625                 630                 635                 640

Gly Thr Pro Ser Asp Pro Val Ser Ala Pro Thr Thr Thr Val Pro Pro
                645                 650                 655

Asn Pro Thr Leu Thr Leu Ala Pro Ser Ser Ser Thr Thr Glu Asp Arg
            660                 665                 670

Thr Thr Ile Thr Thr Ile Ile Thr Thr Ser Tyr Val Thr Val Cys Pro
        675                 680                 685

Thr Gly Phe Thr Thr Val Thr Ile Thr Tyr Thr Thr Thr Tyr Cys Pro
    690                 695                 700

Glu Thr Ala Ser Leu Thr Pro Thr Gln Pro Pro Ile Pro Gly Ala Pro
705                 710                 715                 720

Ala Pro Pro Pro Asp Gly Trp Thr Thr Ile Val Thr Val Cys Pro Gln
                725                 730                 735

Cys Ala Pro Thr Pro Thr Thr Val Thr Leu Thr Val Pro Thr Arg Ser
            740                 745                 750

Ala Phe Leu Pro Ala Arg Thr Glu Thr Arg Pro Val Val Thr Val Val
        755                 760                 765

Pro Val Pro Glu Asn Pro Ile Lys Asn Val Lys Pro Ser Glu Ser Gly
    770                 775                 780

Asp Phe Val Thr Val Thr Thr Ala Ala Pro Ala Thr Val Thr Lys Thr
785                 790                 795                 800

Leu Glu Tyr Asn Asn Pro Val Asp Ser Asp Val Asn Val Gln Pro Thr
                805                 810                 815

Gly Gly Ser Ser Pro Val Glu Phe Glu Gly Ser Ala Met Thr Val Arg
            820                 825                 830

Ser Met Asp Val Val Ala Lys Ala Leu Ile Thr Ala Gly Ala Leu Cys
        835                 840                 845

Trp Asp Cys Ser Trp Gly Tyr Asn Leu Leu Ile Cys
    850                 855                 860
```

<210> SEQ ID NO 4
<211> LENGTH: 6891
<212> TYPE: DNA
<213> ORGANISM: Coccidioides posadasii
<220> FEATURE:
<221> NAME/KEY: misc_feature
<222> LOCATION: 4031, 4239, 4330
<223> OTHER INFORMATION: n = A,T,C or G

<400> SEQUENCE: 4

```
gggccctcta gatgcatgct cgagcggccg ccagtgtgat ggatggccgc agaattcgcc     60

cttccgtcga gggagtctga tagcccttgt ttagtatggg tctctctggc ttgagcctca    120

taatctcttc gtcttcctgt ccctccttaa atctttttta tagagtgata tctccatttc    180

ctctccttgt ccatctgcat tgcagcagcc ataccctgca aacctctggt ttgcgtcctt    240

tccttgagtg cactaccagc ctcacgtcct gttgggccgg cttgcttacc ctcgtttgcc    300

tggagattac tttggcccat ctaccatcct tttaatcatg gggccaacta atattcttgc    360
```

-continued

```
agcgtttatc gctgtgtcct ctctttttat ccagtcactc gctctcaatc cctacgccaa    420
aagtaatttg gcagtctact gggtatgagc caattacttt agcgcccttg gttgtcttga    480
tgctcacctt tctggttgat taggggcaag gagctgggca gaaccggctc agctacttct    540
gcgaaaagac cagctttgat atcattgttg tgggtttcat caatgtgttc cccgaccaag    600
gccccgccgg atggccgggc agcaattttg gaaaccaatg cgccgattcg tattactata    660
caaaaaatgg gacgaagacc aagcttttgg atggctgtta tcagattaag gaagatcttc    720
ccaagtgcaa ggcgctgggg aagacgatcc tgctctccct aggcggagga gccgtgcacg    780
atttctacga ggtcaagagc gaagagtccg ctcttaattt tgcggatttc ctttggggcg    840
cattcggccc actgacacca gactggactg gacctcgtcc attcggagag gcctccctcc    900
agaacgccga gaagaactgg aggggtggtg tcaaggagga gtaagctcct tattgaagtc    960
ggaggacgga gcggtgtcaa gaggatattc ttcgactctg tattatagat aagatgatga   1020
ggaattggag gtagcatagc ttcatttgga tttgctttcc aggctgagac tctagcttgg   1080
agcatagagg gtcctttggc tttcaatatt ctcaagtatc tcgagtttga acttattccc   1140
tgtgaacctt ttattcacca atgagcattg gaatgaacat gaatctgagg actgcaatcg   1200
ccatgaggtt ttcgaaatac atccggatgt cgaaggcttg gggcacctgc gttggttgaa   1260
tttagaacgt ggcactattg atcatccgat agctctgcaa agggcgttgc acaatgcaag   1320
tcaaacgttg ctagcagttc caggtggaat gttatgatga gcattgtatt aaatcaggag   1380
atatagcatg atctctagtt agctcaccac aaaagtcaga cggcgtaacc aaaagtcaca   1440
caacacaagc tgtaaggatt tcggcacggc tacggaagac ggagaagcca ccttcagtgg   1500
actcgagtac catttaattc tatttgtgtt tgatcgagac ctaatacagc ccctacaacg   1560
accatcaaag tcgtatagct accagtgagg aagtggactc aaatcgactt cagcaacatc   1620
tcctggataa actttaagcc taaactatac agaataagat aggtggagag cttataccga   1680
gctcccaaat ctgtccagat catggttgac cggtgcctgg atcttcctat agaatcatcc   1740
ttattcgttg acctagctga ttctggagtg acccagaggg tcatgacttg agcctaaaat   1800
ccgccgcctc caccatttgt agaaaaatgt gacgaactcg tgagctctgt acagtgaccg   1860
gtgactcttt ctggcatgcg gagagacgga cggacgcaga gagaagggct gagtaataag   1920
ccactggcca gacagctctg gcggctctga ggtgcagtgg atgattatta atccgggacc   1980
ggccgcccct ccgccccgaa gtggaaaggc tggtgtgccc ctcgttgacc aagaatctat   2040
tgcatcatcg gagaatatgg agcttcatcg aatcaccggc agtaagcgaa ggagaatgtg   2100
aagccagggg tgtatagccg tcggcgaaat agcatgccat taacctaggt acagaagtcc   2160
aattgcttcc gatctggtaa aagattcacg agatagtacc ttctccgaag taggtagagc   2220
gagtacccgg cgcgtaagct ccctaattgg cccatccggc atctgtaggg cgtccaaata   2280
tcgtgcctct cctgctttgc ccggtgtatg aaaccggaaa ggccgctcag gagctggcca   2340
gcggcgcaga ccgggaacac aagctggcag tcgacccatc cggtgctctg cactcgacct   2400
gctgaggtcc ctcagtccct ggtaggcagc tttgccccgt ctgtccgccc ggtgtgtcgg   2460
cggggttgac aaggtcgttg cgtcagtcca acatttgttg ccatattttc ctgctctccc   2520
caccagctgc tcttttcttt tctctttctt ttcccatctt cagtatattc atcttcccat   2580
ccaagaacct ttatttcccc taagtaagta ctttgctaca tccatactcc atccttccca   2640
tcccttattc ctttgaacct ttcagttcga gctttcccac ttcatcgcag cttgactaac   2700
```

-continued

```
agctaccccg cttgagcaga catcaccatg cctgaactca ccgcgacgtc tgtcgagaag   2760

tttctgatcg aaaagttcga cagcgtctcc gacctgatgc agctctcgga gggcgaagaa   2820

tctcgtgctt tcagcttcga tgtaggaggg cgtggatatg tcctgcgggt aaatagctgc   2880

gccgatggtt tctacaaaga tcgttatgtt tatcggcact ttgcatcggc cgcgctcccg   2940

attccggaag tgcttgacat tggggaattc agcgagagcc tgacctattg catctcccgc   3000

cgtgcacagg gtgtcacgtt gcaagacctg cctgaaaccg aactgcccgc tgttctgcag   3060

ccggtcgcgg aggccatgga tgcgatcgct gcggccgatc ttagccagac gagcgggttc   3120

ggcccattcg gaccgcaagg aatcggtcaa tacactacat ggcgtgattt catatgcgcg   3180

attgctgatc cccatgtgta tcactggcaa actgtgatgg acgacaccgt cagtgcgtcc   3240

gtcgcgcagg ctctcgatga gctgatgctt tgggccgagg actgccccga agtccggcac   3300

ctcgtgcacg cggatttcgg ctccaacaat gtcctgacgg acaatggccg cataacagcg   3360

gtcattgact ggagcgaggc gatgttcggg gattcccaat acgaggtcgc caacatcttc   3420

ttctggaggc cgtggttggc ttgtatggag cagcagacgc gctacttcga gcggaggcat   3480

ccggagcttg caggatcgcc gcggctccgg gcgtatatgc tccgcattgg tcttgaccaa   3540

ctctatcaga gcttggttga cggcaatttc gatgatgcag cttgggcgca gggtcgatgc   3600

gacgcaatcg tccgatccgg agccgggact gtcgggcgta cacaaatcgc ccgcagaagc   3660

gcggccgtct ggaccgatgg ctgtgtagaa gtactcgccg atagtggaaa ccgacgcccc   3720

agcactcgtc cgagggcaaa ggaatagagt agatgccgac cgcgggatcc acttaacgtt   3780

actgaaatca tcaaacagct tgacgaatct ggatataaga tcgttggtgt cgatgtcagc   3840

tccggagttg agacaaatgg tgttcaggat ctcgataaga tacgttcatt tgtccaagca   3900

gcaaagagtg ccttctagtg atttaatagc tccatgtcaa caagaataaa acgcgttttc   3960

gggtttacct cttccagata cagctcatct gcaatgcatt aatgcattga ctgcaaccta   4020

gtaacgcctt ncaggctccg gcgaagagaa gaatagctta gcagagctat tttcattttc   4080

gggagacgag atcaagcaga tcaacggtcg tcaagagacc tacgagactg aggaatccgc   4140

tcttggctcc acgcgactat atatttgtct ctaattgtac tttgacatgc tcctcttctt   4200

tactctgata gcttgactat gaaaattccg tcaccagcnc ctgggttcgc aaagataatt   4260

gcatgtttct tccttgaact ctcaagccta caggacacac attcatcgta ggtataaacc   4320

tcgaaatcan ttcctactaa gatggtatac aatagtaacc atgcatggtt gcctagtgaa   4380

tgctccgtaa cacccaatac gccggccgaa actttttac aactctccta tgagtcgttt   4440

acccagaatg cacaggtaca cttgtttaga ggtaatcctt ctttctagta caagcagcca   4500

ggattcacca tccacgacaa tttcgacgaa gtctgcgccc actggcactg tcacaactag   4560

gagtcaggat ttaccctcaa cgaccatctc tacgagatct cctgagactg aaactgagac   4620

tgcaacaaca aaaagtcagg gttcaccgtc aattactctc tctacaaggt cttcctccgc   4680

tgagactgta tcaacaagaa gtcagcattc atcgtctaca acaatttcaa cgaagtctgc   4740

accaactgag actggtacga caagtgaaca ttcaacatca atgcctgtct ctacgagatc   4800

ggcttccacc gagactgtaa taacgagaag tcagaattca gattctcaat caatgacagt   4860

ctctacaaga tcgccttcca ccgaaagtat cacaacaaga agtcaaggtt cgccatcaga   4920

gacattttca accaagtctg ttccagtaga taccatctca actgaattgc cttctcaaac   4980

gccaacaacg attataacgg gaacaccttc tgatcctgta tcagccccga ccaccacggt   5040

tcctcccaat cctaccctga cgctcgcccc atcttcctcc acaacagaag accgcaccac   5100
```

-continued aatcactact ataatcacca catcctacgt cactgtctgt cccactggct ttaccacggt 5160
cacaataaca tacaccacca cctactgccc ggagaccgct tcgctcacgc caactcagcc 5220
ccctattccg ggagctccag cccctccacc agatggctgg acaacaattg tcaccgtgtg 5280
cccccagtgc gccccaacgc caactaccgt cacactcacg gtccccacaa gatctgcctt 5340
ccttcccgca cgcacggaga ctcgccctgt tgtcactgtg gtcccagtgc cggagaatcc 5400
aattaagaac gtgaagccta gtgagtccgg agattttgtg actgttacta cagcggcgcc 5460
ggcaacggtt acaaagacgt tggaatacaa caacccggtg gattccgatg tgaatgtcca 5520
acccacgggt ggtagttccc ccgtcgagtt tgaaggcagt gcgatgactg taagaagtat 5580
ggatgtggtc gcgaaagccc tgattaccgc tggagcgctg tgttgggatt gttcttgggg 5640
ttataatctg ttaatttgct gaggcgatat atacacattt tcttcggagg ggtgtgtaca 5700
taatgtcacg ggtgctgtac ttgtacatac aagggcgaat tccagcacac tggcggccat 5760
ctgcagaatt agcttggcgt aatcatggtc atagctgttt cctgtgtgaa attgttatcc 5820
gctcacaatt ccacacaaca tacgagccgg aagcataaag tgtaaagcct ggggtgccta 5880
atgagtgagc taactcacat taattgcgtt gcgctcactg cccgctttcc agtcgggaaa 5940
cctgtcgtgc cagctgcatt aatgaatcgg ccaacgcgcg gggagaggcg gtttgcgtat 6000
tgggcgctct tccgcttcct cgctcactga ctcgctgcgc tcggtcgttc ggctgcggcg 6060
agcggtatca gctcactcaa aggcggtaat acggttatcc acagaatcag gggataacgc 6120
aggaaagaac atgtgagcaa aaggccagca aaaggccagg aaccgtaaaa aggccgcgtt 6180
gctggcgttt ttccataggc tccgcccccc tgacgagcat cacaaaaatc gacgctcaag 6240
tcagaggtgg cgaaacccga caggactata aagataccag gcgtttcccc ctggaagctc 6300
cctcgtgcgc tctcctgttc cgaccctgcc gcttaccgga tacctgtccg cctttctccc 6360
ttcgggaagc gtggcgcttt ctcatagctc acgctgtagg tatctcagtt cggtgtaggt 6420
cgttcgctcc aagctgggct gtgtgcacga accccccgtt cagcccgacc gctgcgcctt 6480
atccggtaac tatcgtcttg agtccaaccc ggtaagacac gacttatcgc cactggcagc 6540
agccactggt aacaggatta gcagagcgag gtatgtaggc ggtgctacag agttcttgaa 6600
gtggtggcct aactacggct acactagaag aacagtattt ggtatctgcg ctctgctgaa 6660
gccagttacc ttcggaaaaa gagttggtag ctcttgatcc ggcaaacaaa ccaccgctgg 6720
tagcggtggt ttttttgttt gcaagcagca gattacgcgc agaaaaaaag gatctcaaga 6780
agatcctttg atcttttcta cggggtctga cgctcagtgg aacgaaaact cacgttaagg 6840
gattttggtc atgagattat caaaaaggat cttcacctag atccttttaa a 6891

<210> SEQ ID NO 5
<211> LENGTH: 967
<212> TYPE: DNA
<213> ORGANISM: Coccidioides posadasii

<400> SEQUENCE: 5
cctcagtcga tggatttgac ttcgatatcg aaaagggtag taactttggt atgtatcccg 60
ttctcccttc caggtgattc gagtccctga ctgacgaaag taggctattc aattatggtc 120
cgacgtttgc gagaactttt cctccaggac ccgctcaaca gatactatat ctctgcagcc 180
ccccagtgca taatgccaga taagtatctc tcacatgcga tatctaattc ggcgttcgac 240
ttcatcttca tccagttcta caacaatcct tcgtgctctg ccaaacggtg ggtgactaac 300

-continued

```
cccaagtccg tgacgtacac cgtggacgat tgggtcaaat acatccgcaa aagcggaaac    360

ccattagcga aacttttcat tggccttccc gcatctaagt ctgctgctgc gaaagaagac    420

tatcttactc ctggtgaagc caccaaaatc gtcagcacgt acatggcgaa atatccaagt    480

acttttggtg gtatgatggt gtgggaagca actgcatcgg agaacaataa gcttggcgga    540

cttccatacg ccgatataat gaaggaagtg ctgttgcgat gcgatccgga tccccctacc    600

agtactgtta caagtaccac atctgcctcg acttcaaccc agacttcatc tcaaagcact    660

actatggaaa ccaagacttt gtcggcttct acgaccccga gcagtccgag tactgtgtcg    720

ccaagttcaa caatgcagac aacctctact ggttcaactt ccattgagac tgtcacaacg    780

agaagtcaag agccaccatc aacaacaatc tccacaaggt cagcttccac tgagcctgta    840

acaacgagaa gtcaagagcc accatcaacc acaatctcca caaggtcagc ttccactgag    900

actgtgacga caagaagtca agagccacca tcaaccacaa tctccacatg gtcggcctcc    960

actgaaa                                                              967
```

<210> SEQ ID NO 6
<211> LENGTH: 3018
<212> TYPE: DNA
<213> ORGANISM: Coccidioides posadasii

<400> SEQUENCE: 6

```
gtgcgctgta agaccatgat cacttcattt gatggcccta actggagacg cttcttttag     60

caccaacatg tggcactttg tacttgacat cagcaccgcg caccctgtgc tcaccggctg    120

actagtgata ctttagggca aagtggtggg gatcctggcg gttccggggc tcgtcccttg    180

cctagaaaca ttcccgcatg gtatatacgt aggaaaccgg gcaaagttgg taattacctt    240

ggttcactca atgtcatagt catctggccc ttcaacgcag gaatttcaga ccatatgtat    300

aacagctcat attgacctgg gaaactctcc aagaaatgct aacatttgag ccatttatca    360

tcatctacca tcactatcta ctgctaattg gtttccggca atttctctca gtcttacatt    420

cctcacagct ccagcatgat gaactccact ggtcaacatc aaaatgctta cccgaatttt    480

agcttgcgag ggagagtata tatcgtcact gggggcggca gggggctagg attagtgatg    540

gcagaggcaa taactgaggc aggtgcggaa ggtaaggatg atcaatttcg actgtgagtg    600

gcccttattg atgaagctaa tggccgttct agttcactgt tttgatatcc taccagaacc    660

cgatgatgaa ttcgttcgga cacaggagct cgccagcaag gcacacgtcg gcaatctgca    720

ctatcatcat gtggacgtga gagactcgaa gcatctcaac gatgttgtgg agaagatcgc    780

attgcgcagt aatcgcctag acggactagt cgcagctgct ggagtacagc aagtgaccga    840

agcaatcgac tacaccgccg acgatgtaac gaagatgctg gatataaact atactggtgt    900

ttttatgacc gctcaagcca cggctcgcca aatgatgaaa ctcggctgca atggttccat    960

agtcctggtg gctagcatga gcgggattgt ggccaacaaa ggccttaatt cacccgtata   1020

caactcctca aaagccgcag taatccaact aggacgaaac ctggccatgg agtggggttc   1080

caaaggtatt cgagtgaact cgctttgccc gggccacgtc atcacgccga tggtagaaaa   1140

gaattttgaa gaagtaccgg acctaaagaa gacttgggaa aaagagagca tgcttgggag   1200

attatccagg ccagaggaat tcactggcgc tgtcattttc atgttaagcg atgcaagctc   1260

ttatatgacc ggcagcagtc ttgtgatcga tggtggacat acagcatggt gatttcagtc   1320

gtataatgct attatgagtt cacgtatacc tttggtagta cggagttttt ttcgatggcc   1380

tgttgatgga gcattgcatc tcaatcgaaa cctcctccta catgcactta ttagttatgt   1440
```

-continued

```
actaacttgg gctgaatttg ttgaaccgaa ttattagtgc agttcctgca gtatgccgta   1500

taattccaga taggctgtca gcaattcaat atctacatac gattcagggg tagctccaag   1560

gctgtgcgtt catgcaaaat tcgtaaacaa aattaagatg ggagaaagcg tgcgaaacaa   1620

tgatgtagaa gatgatgcaa gcgggcgagg aagtccgggg taactacgga gtagttactc   1680

cgtagttagt ggggcgttac aactcgaaca atgacaagca gcctgctccc agcacaaccc   1740

cttaaagctg gtttaacctt ccgagatatc aggtacagca gtctttccgt ggagttactt   1800

ttacggaaac gaactcgaag cccactacgg agtatttagg aggcatatca tgcttcggtg   1860

aagcgagcag cacctgggag atcagttata tacgaaaata caaacccagt tactcaagcg   1920

cccgtcggat tttaccgagt agttgaatca aaagagctca ctatctggtc gaatagacga   1980

tatcggaggc gctgaggacg atttgaccaa tgcctccaat tccggaaagc cacggtaaca   2040

gcacattgac gaatcctcga gtgatatgtt actatcaaac ctattatcct aacaatggga   2100

ccgactacat ttctaccctc ccgcttctga cgaatgactg tggggtgtcg cacattattc   2160

ttgccgcaat tcatatcaat gatgaacccg gaaatattac actcaacgac cattccccag   2220

acgatccccg gtacgtgccg ttgtgggcag agatgcgcgt aatgcaggcg agtgggacca   2280

aggtgatggg gatggttggg ggtgccgcca aaggcagtta tcagaggctt gatggaagcg   2340

tggcagattt tgaagcgttc tactgcccgc tccgtgatat gatacgaacg cggaatttga   2400

atggcctgga cctcgacgta gaggaggata tgtccctcga cggcattatt cgcctgattg   2460

atcgcctcaa atcggatttt ggagatgagt ttatcatcac cctagctccc gtggccactg   2520

ctatggtgcg tggcctgaga catctctccg gctttgatta ccgagcattg gagactgcca   2580

ggggctcaaa aatatcttgg tataatgtgc agttctacaa tggacggggt catatgctgc   2640

atcccagcgt ctacgatacc atcatacatc aaggctggga ggcggagagg atcgttatag   2700

gtctcttgac caatcccgct aacgggtctc agggctatgt tccaatggaa acgataagtt   2760

cggtgttagc aaacgtgctg acaaagtacc catcgttcgg gggggtatca gggtgggaat   2820

acttcaacgc aatgccgggg ggcatctctc gcccatggga atgggccgct tcaatctcac   2880

tgatagtggg aatgaagaca gtccttgcgt gtgcgacttc tgcgctttac tcgaagttag   2940

ccacggcata gagttttatg ataaacggaa gatattctta gtagaaacta gaacaaggac   3000

gatagacttg agttcttg                                                 3018
```

<210> SEQ ID NO 7
<211> LENGTH: 942
<212> TYPE: DNA
<213> ORGANISM: Coccidioides posadasii

<400> SEQUENCE: 7

```
atgcctccaa ttccggaaag ccacggtaac agcacattga cgaatcctcg agtgatatgt     60

tactatcaaa cctattatcc taacaatggg accgactaca tttctaccct cccgcttctg    120

acgaatgact gtggggtgtc gcacattatt cttgccgcaa ttcatatcaa tgatgaaccc    180

ggaaatatta cactcaacga ccattcccca gacgatcccc ggtacgtgcc gttgtgggca    240

gagatgcgcg taatgcaggc gagtgggacc aaggtgatgg ggatggttgg gggtgccgcc    300

aaaggcagtt atcagaggct tgatggaagc gtggcagatt ttgaagcgtt ctactgcccg    360

ctccgtgata tgatacgaac gcggaatttg aatggcctgg acctcgacgt agaggaggat    420

atgtccctcg acggcattat tcgcctgatt gatcgcctca aatcggattt tggagatgag    480
```

-continued

```
tttatcatca ccctagctcc cgtggccact gctatggtgc gtggcctgag acatctctcc    540

ggctttgatt accgagcatt ggagactgcc aggggctcaa aaatatcttg gtataatgtg    600

cagttctaca atggacgggg tcatatgctg catcccagcg tctacgatac catcatacat    660

caaggctggg aggcggagag gatcgttata ggtctcttga ccaatcccgc taacgggtct    720

cagggctatg ttccaatgga aacgataagt tcggtgttag caaacgtgct gacaaagtac    780

ccatcgttcg ggggggtatc agggtgggaa tacttcaacg caatgccggg gggcatctct    840

cgcccatggg aatgggccgc ttcaatctca ctgatagtgg gaatgaagac agtccttgcg    900

tgtgcgactt ctgcgcttta ctcgaagtta gccacggcat ag                       942
```

<210> SEQ ID NO 8
<211> LENGTH: 313
<212> TYPE: PRT
<213> ORGANISM: Coccidioides posadasii

<400> SEQUENCE: 8

```
Met Pro Pro Ile Pro Glu Ser His Gly Asn Ser Thr Leu Thr Asn Pro
 1               5                  10                  15

Arg Val Ile Cys Tyr Tyr Gln Thr Tyr Tyr Pro Asn Asn Gly Thr Asp
            20                  25                  30

Tyr Ile Ser Thr Leu Pro Leu Leu Thr Asn Asp Cys Gly Val Ser His
        35                  40                  45

Ile Ile Leu Ala Ala Ile His Ile Asn Asp Glu Pro Gly Asn Ile Thr
    50                  55                  60

Leu Asn Asp His Ser Pro Asp Asp Pro Arg Tyr Val Pro Leu Trp Ala
65                  70                  75                  80

Glu Met Arg Val Met Gln Ala Ser Gly Thr Lys Val Met Gly Met Val
                85                  90                  95

Gly Gly Ala Ala Lys Gly Ser Tyr Gln Arg Leu Asp Gly Ser Val Ala
            100                 105                 110

Asp Phe Glu Ala Phe Tyr Cys Pro Leu Arg Asp Met Ile Arg Thr Arg
        115                 120                 125

Asn Leu Asn Gly Leu Asp Leu Asp Val Glu Glu Asp Met Ser Leu Asp
    130                 135                 140

Gly Ile Ile Arg Leu Ile Asp Arg Leu Lys Ser Asp Phe Gly Asp Glu
145                 150                 155                 160

Phe Ile Ile Thr Leu Ala Pro Val Ala Thr Ala Met Val Arg Gly Leu
                165                 170                 175

Arg His Leu Ser Gly Phe Asp Tyr Arg Ala Leu Glu Thr Ala Arg Gly
            180                 185                 190

Ser Lys Ile Ser Trp Tyr Asn Val Gln Phe Tyr Asn Gly Arg Gly His
        195                 200                 205

Met Leu His Pro Ser Val Tyr Asp Thr Ile Ile His Gln Gly Trp Glu
    210                 215                 220

Ala Glu Arg Ile Val Ile Gly Leu Leu Thr Asn Pro Ala Asn Gly Ser
225                 230                 235                 240

Gln Gly Tyr Val Pro Met Glu Thr Ile Ser Ser Val Leu Ala Asn Val
                245                 250                 255

Leu Thr Lys Tyr Pro Ser Phe Gly Gly Val Ser Gly Trp Glu Tyr Phe
            260                 265                 270

Asn Ala Met Pro Gly Gly Ile Ser Arg Pro Trp Glu Trp Ala Ala Ser
        275                 280                 285

Ile Ser Leu Ile Val Gly Met Lys Thr Val Leu Ala Cys Ala Thr Ser
```

-continued

```
    290                 295                 300

Ala Leu Tyr Ser Lys Leu Ala Thr Ala
305                 310


<210> SEQ ID NO 9
<211> LENGTH: 813
<212> TYPE: DNA
<213> ORGANISM: Coccidioides posadasii

<400> SEQUENCE: 9

atgaactcca ctggtcaaca tcaaaatgct tacccgaatt ttagcttgcg agggagagta      60

tatatcgtca ctgggggcgg cagggggcta ggattagtga tggcagaggc aataactgag     120

gcaggtgcgg aagttcactg ttttgatatc ctaccagaac ccgatgatga attcgttcgg     180

acacaggagc tcgccagcaa ggcacacgtc ggcaatctgc actatcatca tgtggacgtg     240

agagactcga agcatctcaa cgatgttgtg gagaagatcg cattgcgcag taatcgccta     300

gacggactag tcgcagctgc tggagtacag caagtgaccg aagcaatcga ctacaccgcc     360

gacgatgtaa cgaagatgct ggatataaac tatactggtg tttttatgac cgctcaagcc     420

acggctcgcc aaatgatgaa actcggctgc aatggttcca tagtcctggt ggctagcatg     480

agcgggattg tggccaacaa aggccttaat tcacccgtat acaactcctc aaaagccgca     540

gtaatccaac taggacgaaa cctggccatg gagtggggtt ccaaaggtat tcgagtgaac     600

tcgctttgcc cgggccacgt catcacgccg atggtagaaa agaattttga agaagtaccg     660

gacctaaaga agacttggga aaaagagagc atgcttggga gattatccag gccagaggaa     720

ttcactggcg ctgtcatttt catgttaagc gatgcaagct cttatatgac cggcagcagt     780

cttgtgatcg atggtggaca tacagcatgg tga                                  813


<210> SEQ ID NO 10
<211> LENGTH: 270
<212> TYPE: PRT
<213> ORGANISM: Coccidioides posadasii

<400> SEQUENCE: 10

Met Asn Ser Thr Gly Gln His Gln Asn Ala Tyr Pro Asn Phe Ser Leu
 1               5                  10                  15

Arg Gly Arg Val Tyr Ile Val Thr Gly Gly Gly Arg Gly Leu Gly Leu
            20                  25                  30

Val Met Ala Glu Ala Ile Thr Glu Ala Gly Ala Glu Val His Cys Phe
        35                  40                  45

Asp Ile Leu Pro Glu Pro Asp Asp Glu Phe Val Arg Thr Gln Glu Leu
    50                  55                  60

Ala Ser Lys Ala His Val Gly Asn Leu His Tyr His His Val Asp Val
65                  70                  75                  80

Arg Asp Ser Lys His Leu Asn Asp Val Val Glu Lys Ile Ala Leu Arg
                85                  90                  95

Ser Asn Arg Leu Asp Gly Leu Val Ala Ala Ala Gly Val Gln Gln Val
            100                 105                 110

Thr Glu Ala Ile Asp Tyr Thr Ala Asp Asp Val Thr Lys Met Leu Asp
        115                 120                 125

Ile Asn Tyr Thr Gly Val Phe Met Thr Ala Gln Ala Thr Ala Arg Gln
    130                 135                 140

Met Met Lys Leu Gly Cys Asn Gly Ser Ile Val Leu Val Ala Ser Met
145                 150                 155                 160
```

-continued

```
Ser Gly Ile Val Ala Asn Lys Gly Leu Asn Ser Pro Val Tyr Asn Ser
                165                 170                 175

Ser Lys Ala Ala Val Ile Gln Leu Gly Arg Asn Leu Ala Met Glu Trp
            180                 185                 190

Gly Ser Lys Gly Ile Arg Val Asn Ser Leu Cys Pro Gly His Val Ile
        195                 200                 205

Thr Pro Met Val Glu Lys Asn Phe Glu Glu Val Pro Asp Leu Lys Lys
    210                 215                 220

Thr Trp Glu Lys Glu Ser Met Leu Gly Arg Leu Ser Arg Pro Glu Glu
225                 230                 235                 240

Phe Thr Gly Ala Val Ile Phe Met Leu Ser Asp Ala Ser Ser Tyr Met
                245                 250                 255

Thr Gly Ser Ser Leu Val Ile Asp Gly Gly His Thr Ala Trp
            260                 265                 270


<210> SEQ ID NO 11
<211> LENGTH: 4967
<212> TYPE: DNA
<213> ORGANISM: Coccidioides posadasii
<220> FEATURE:
<221> NAME/KEY: misc_feature
<222> LOCATION: 3128, 3336, 3427
<223> OTHER INFORMATION: n = A,T,C or G

<400> SEQUENCE: 11

gggccctcta gatgcatgct cgagcggccg ccagtgtgat ggatatctgc agaattcgcc     60

cttgtgcgct gtaagaccat gatcacttca tttgatggcc ctaactggag acgcttcttt    120

tagcaccaac atgtggcact ttgtacttga catcagcacc gcgcaccctg tgctcaccgg    180

ctgactagtg atactttagg gcaaagtggt ggggatcctg gcggttccgg ggctcgtccc    240

ttgcctagaa acattcccgc atggtatata cgtaggaaac cgggcaaagt tggtaattac    300

cttggttcac tcaatgtcat agtcatctgg cccttcaacg caggaatttc agaccatatg    360

tataacagct catattgacc tgggaaactc tccaagaaat gctaacattt gagccattta    420

tcatcatcta ccatcactat ctactgctaa ttggtttccg gcaatttctc tcagtcttac    480

attcctcaca gctccagcat gatgaactcc actggtcaac atcaaaatgc ttacccgaat    540

tttagcttgc gagggagagt atatatcgtc actgggggcg gcagggggct aggattagtg    600

atggcagagg caataactga ggcaggtgcg gaaggtaagg atgatcaatt tcgactgtga    660

gtggccctta ttgatgaagc taatggccgt tctagttcac tgttttgata tcctaccaga    720

acccgatgat gaattcgttc ggacacagga gctcgccagc aaggcacacg tcggcaatct    780

gcactatcat catgtggacg tgagagactc gaagcatctc aacgatgttg tggagaagat    840

cgcattgcgc agtaatcgcc tagacggact agtcgcagct gctggagtac agcaagtgac    900

cgaagcaatc gactacaccg ccgacgatgt aacgaagatg ctggatataa actatactgg    960

tgtttttatg accgctcaag ccacggctcg ccaaatgatg aaactcggct gcaatggttc   1020

catagtcctg gtggctagca gttccaggtg gaatgttatg atgagcattg tattaaatca   1080

ggagatatag catgatctct agttagctca ccacaaaagt cagacggcgt aaccaaaagt   1140

cacacaacac aagctgtaag gatttcggca cggctacgga agacggagaa gccaccttca   1200

gtggactcga gtaccattta attctatttg tgtttgatcg agacctaata cagcccctac   1260

aacgaccatc aaagtcgtat agctaccagt gaggaagtgg actcaaatcg acttcagcaa   1320

catctcctgg ataaacttta agcctaaact atacagaata agataggtgg agagcttata   1380
```

-continued

```
ccgagctccc aaatctgtcc agatcatggt tgaccggtgc ctggatcttc ctatagaatc   1440
atccttattc gttgacctag ctgattctgg agtgacccag agggtcatga cttgagccta   1500
aaatccgccg cctccaccat ttgtagaaaa atgtgacgaa ctcgtgagct ctgtacagtg   1560
accggtgact ctttctggca tgcggagaga cggacggacg cagagagaag ggctgagtaa   1620
taagccactg gccagacagc tctggcggct ctgaggtgca gtggatgatt attaatccgg   1680
gaccggccgc ccctccgccc cgaagtggaa aggctggtgt gcccctcgtt gaccaagaat   1740
ctattgcatc atcggagaat atggagcttc atcgaatcac cggcagtaag cgaaggagaa   1800
tgtgaagcca ggggtgtata gccgtcggcg aaatagcatg ccattaacct aggtacagaa   1860
gtccaattgc ttccgatctg gtaaaagatt cacgagatag taccttctcc gaagtaggta   1920
gagcgagtac ccggcgcgta agctccctaa ttggcccatc cggcatctgt agggcgtcca   1980
aatatcgtgc ctctcctgct ttgcccggtg tatgaaaccg gaaaggccgc tcaggagctg   2040
gccagcggcg cagaccggga acacaagctg gcagtcgacc catccggtgc tctgcactcg   2100
acctgctgag gtccctcagt ccctggtagg cagctttgcc ccgtctgtcc gcccggtgtg   2160
tcggcggggt tgacaaggtc gttgcgtcag tccaacattt gttgccatat tttcctgctc   2220
tccccaccag ctgctctttt cttttctctt tcttttccca tcttcagtat attcatcttc   2280
ccatccaaga acctttattt cccctaagta agtactttgc tacatccata ctccatcctt   2340
cccatccctt attcctttga acctttcagt tcgagctttc ccacttcatc gcagcttgac   2400
taacagctac cccgcttgag cagacatcac catggccaag ttgaccagtg ccgttccggt   2460
gctcaccgcg cgcgacgtcg ccggagcggt cgagttctgg accgaccggc tcgggttctc   2520
ccgggacttc gtggaggacg acttcgccgg tgtggtccgg gacgacgtga ccctgttcat   2580
cagcgcggtc caggaccagg tggtgccgga caacaccctg gcctgggtgt gggtgcgcgg   2640
cctggacgag ctgtacgccg agtggtcgga ggtcgtgtcc acgaacttcc gggacgcctc   2700
cgggccggcc atgaccgaga tcggcgagca gccgtggggg cgggagttcg ccctgcgcga   2760
cccggccggc aactgcgtgc acttcgtggc cgaggagcag gactgaccga cgccgaccaa   2820
caccgccggt ccgacggcgg cccacgggtc ccaggagctt gagatccact taacgttact   2880
gaaatcatca aacagcttga cgaatctgga tataagatcg ttggtgtcga tgtcagctcc   2940
ggagttgaga caaatggtgt tcaggatctc gataagatac gttcatttgt ccaagcagca   3000
aagagtgcct tctagtgatt taatagctcc atgtcaacaa gaataaaacg cgttttcggg   3060
tttacctctt ccagatacag ctcatctgca atgcattaat gcattgactg caacctagta   3120
acgccttnca ggctccggcg aagagaagaa tagcttagca gagctatttt cattttcggg   3180
agacgagatc aagcagatca acggtcgtca agagacctac gagactgagg aatccgctct   3240
tggctccacg cgactatata tttgtctcta attgtacttt gacatgctcc tcttctttac   3300
tctgatagct tgactatgaa aattccgtca ccagcncctg ggttcgcaaa gataattgca   3360
tgtttcttcc ttgaactctc aagcctacag gacacacatt catcgtaggt ataaacctcg   3420
aaatcanttc ctactaagat ggtatacaat agtaaccatg catggttgcc tagtgaatgc   3480
tccgtaacac ccaatacgcc ggccgaaact tttttacaac tctcctatga gtcgtttacc   3540
cagaatgcac aggtacactt gtttagaggt aatccttctt tctagagctt ggcactggcc   3600
gtcgttttac aacgtcgtga ctgggaaaac cctggcgtta cccaacttaa tcgccttgca   3660
gcacatcccc ctttcgccag ctggcgtaat agcgaagagg cccgcaccga tcgcccttcc   3720
caacagttgc gcagcctgaa tggcgaatgg cgcctgatgc ggtattttct ccttacgcat   3780
```

-continued ctgtgcggta tttcacaccg catatggtgc actctcagta caatctgctc tgatgccgca 3840
tagttaagcc agccccgaca cccgccaaca cccgctgacg cgccctgacg ggcttgtctg 3900
ctcccggcat ccgcttacag acaagctgtg accgtctccg ggagctgcat gtgtcagagg 3960
ttttcaccgt catcaccgaa acgcgcgaga cgaaagggcc tcgtgatacg cctattttta 4020
taggttaatg tcatgataat aatggtttct tagacgtcag gtggcacttt tcggggaaat 4080
gtgcgcggaa cccctatttg tttatttttc taaatacatt caaatatgta tccgctcatg 4140
agacaataac cctgataaat gcttcaataa tattacactc aacgaccatt ccccagacga 4200
tccccggtac gtgccgttgt gggcagagat gcgcgtaatg caggcgagtg ggaccaaggt 4260
gatggggatg gttgggggtg ccgccaaagg cagttatcag aggcttgatg gaagcgtggc 4320
agattttgaa gcgttctact gcccgctccg tgatatgata cgaacgcgga atttgaatgg 4380
cctggacctc gacgtagagg aggatatgtc cctcgacggc attattcgcc tgattgatcg 4440
cctcaaatcg gattttggag atgagtttat catcacccta gctcccgtgg ccactgctat 4500
ggtgcgtggc ctgagacatc tctccggctt tgattaccga gcattggaga ctgccagggg 4560
ctcaaaaata tcttggtata atgtgcagtt ctacaatgga cggggtcata tgctgcatcc 4620
cagcgtctac gataccatca tacatcaagg ctgggaggcg gagaggatcg ttataggtct 4680
cttgaccaat cccgctaacg ggtctcaggg ctatgttcca atggaaacga taagttcggt 4740
gttagcaaac gtgctgacaa agtacccatc gttcgggggg gtatcagggt gggaatactt 4800
caacgcaatg ccggggggca tctctcgccc atgggaatgg gccgcttcaa tctcactgat 4860
agtgggaatg aagacagtcc ttgcgtgtgc gacttctgcg ctttactcga agaagggcga 4920
attccagcac actggcggcc gttactagtg gatccgagct cggtacc 4967

<210> SEQ ID NO 12
<211> LENGTH: 1224
<212> TYPE: DNA
<213> ORGANISM: Coccidioides posadasii
<400> SEQUENCE: 12
ctagcatgag cgggattgtg gccaacaaag gccttaattc acccgtatac aactcctcaa 60
aagccgcagt aatccaacta ggacgaaacc tggccatgga gtggggttcc aaaggtattc 120
gagtgaactc gctttgcccg ggccacgtca tcacgccgat ggtagaaaag aattttgaag 180
aagtaccgga cctaaagaag acttgggaaa aagagagcat gcttgggaga ttatccaggc 240
cagaggaatt cactggcgct gtcattttca tgttaagcga tgcaagctct tatatgaccg 300
gcagcagtct tgtgatcgat ggtggacata cagcatggtg atttcagtcg tataatgcta 360
ttatgagttc acgtatacct ttggtagtac ggagtttttt tcgatggcct gttgatggag 420
cattgcatct caatcgaaac ctcctcctac atgcacttat tagttatgta ctaacttggg 480
ctgaatttgt tgaaccgaat tattagtgca gttcctgcag tatgccgtat aattccagat 540
aggctgtcag caattcaata tctacatacg attcaggggt agctccaagg ctgtgcgttc 600
atgcaaaatt cgtaaacaaa attaagatgg gagaaagcgt gcgaaacaat gatgtagaag 660
atgatgcaag cgggcgagga agtccggggt aactacggag tagttactcc gtagttagtg 720
gggcgttaca actcgaacaa tgacaagcag cctgctccca gcacaacccc ttaaagctgg 780
tttaaccttc cgagatatca ggtacagcag tctttccgtg gagttacttt tacggaaacg 840
aactcgaagc ccactacgga gtatttagga ggcatatcat gcttcggtga agcgagcagc 900

-continued

```
acctgggaga tcagttatat acgaaaatac aaacccagtt actcaagcgc ccgtcggatt     960

ttaccgagta gttgaatcaa aagagctcac tatctggtcg aatagacgat atcggaggcg    1020

ctgaggacga tttgaccaat gcctccaatt ccggaaagcc acggtaacag cacattgacg    1080

aatcctcgag tgatatgtta ctatcaaacc tattatccta acaatgggac cgactacatt    1140

tctaccctcc cgcttctgac gaatgactgt ggggtgtcgc acattattct tgccgcaatt    1200

catatcaatg atgaacccgg aaat                                           1224


<210> SEQ ID NO 13
<211> LENGTH: 5667
<212> TYPE: DNA
<213> ORGANISM: Coccidioides posadasii
<220> FEATURE:
<221> NAME/KEY: misc_feature
<222> LOCATION: 3968, 4176, 4267
<223> OTHER INFORMATION: n = A,T,C or G

<400> SEQUENCE: 13

ccgtcgaggg agtctgatag cccttgttta gtatgggtct ctctggcttg agcctcataa      60

tctcttcgtc ttcctgtccc tccttaaatc ttttttatag agtgatatct ccatttcctc     120

tccttgtcca tctgcattgc agcagccata ccctgcaaac ctctggtttg cgtcctttcc     180

ttgagtgcac taccagcctc acgtcctgtt gggccggctt gcttaccctc gtttgcctgg     240

agattacttt ggcccatcta ccatcctttt aatcatgggg ccaactaata ttcttgcagc     300

gtttatcgct gtgtcctctc tttttatcca gtcactcgct ctcaatccct acgccaaaag     360

taatttggca gtctactggg tatgagccaa ttactttagc gcccttggtt gtcttgatgc     420

tcacctttct ggttgattag gggcaaggag ctgggcagaa ccggctcagc tacttctgcg     480

aaaagaccag ctttgatatc attgttgtgg gtttcatcaa tgtgttcccc gaccaaggcc     540

ccgccggatg gccgggcagc aattttggaa accaatgcgc cgattcgtat tactatacaa     600

aaaatgggac gaagaccaag cttttggatg gctgttatca gattaaggaa gatcttccca     660

agtgcaaggc gctggggaag acgatcctgc tctccctagg cggaggagcc gtgcacgatt     720

tctacgaggt caagagcgaa gagtccgctc ttaattttgc ggatttcctt tggggcgcat     780

tcggcccact gacaccagac tggactggac ctcgtccatt cggagaggcc tccctccaga     840

acgccgagaa gaactggagg ggtggtgtca aggaggagta agctccttat tgaagtcgga     900

ggacggagcg gtgtcaagag gatattcttc gactctgtat tatagataag atgatgagga     960

attggaggta gcatagcttc atttggattt gctttccagg ctgagactct agcttggagc    1020

atagagggtc ctttggcttt caatattctc aagtatctcg agtttgaact tattccctgt    1080

gaacctttta ttcaccaatg agcattggaa tgaacatgaa tctgaggact gcaatcgcca    1140

tgaggttttc gaaatacatc cggatgtcga aggcttgggg cacctgcgtt ggttgaattt    1200

agaacgtggc actattgatc atccgatagc tctgcaaagg gcgttgcaca atgcaagtca    1260

aacgttgcta gcagttccag gtggaatgtt atgatgagca ttgtattaaa tcaggagata    1320

tagcatgatc tctagttagc tcaccacaaa agtcagacgg cgtaaccaaa agtcacacaa    1380

cacaagctgt aaggatttcg gcacggctac ggaagacgga gaagccacct tcagtggact    1440

cgagtaccat ttaattctat ttgtgtttga tcgagaccta atacagcccc tacaacgacc    1500

atcaaagtcg tatagctacc agtgaggaag tggactcaaa tcgacttcag caacatctcc    1560

tggataaact ttaagcctaa actatacaga ataagatagg tggagagctt ataccgagct    1620

cccaaatctg tccagatcat ggttgaccgg tgcctggatc ttcctataga atcatcctta    1680
```

-continued

```
ttcgttgacc tagctgattc tggagtgacc cagagggtca tgacttgagc ctaaaatccg   1740
ccgcctccac catttgtaga aaaatgtgac gaactcgtga gctctgtaca gtgaccggtg   1800
actctttctg gcatgcggag agacggacgg acgcagagag aagggctgag taataagcca   1860
ctggccagac agctctggcg gctctgaggt gcagtggatg attattaatc cgggaccggc   1920
cgcccctccg ccccgaagtg gaaaggctgg tgtgcccctc gttgaccaag aatctattgc   1980
atcatcggag aatatggagc ttcatcgaat caccggcagt aagcgaagga gaatgtgaag   2040
ccaggggtgt atagccgtcg gcgaaatagc atgccattaa cctaggtaca gaagtccaat   2100
tgcttccgat ctggtaaaag attcacgaga tagtaccttc tccgaagtag gtagagcgag   2160
tacccggcgc gtaagctccc taattggccc atccggcatc tgtagggcgt ccaaatatcg   2220
tgcctctcct gctttgcccg gtgtatgaaa ccggaaaggc cgctcaggag ctggccagcg   2280
gcgcagaccg ggaacacaag ctggcagtcg acccatccgg tgctctgcac tcgacctgct   2340
gaggtccctc agtccctggt aggcagcttt gccccgtctg tccgcccggt gtgtcggcgg   2400
ggttgacaag gtcgttgcgt cagtccaaca tttgttgcca tattttcctg ctctccccac   2460
cagctgctct tttcttttct ctttcttttc ccatcttcag tatattcatc ttcccatcca   2520
agaaccttta tttcccctaa gtaagtactt tgctacatcc atactccatc cttcccatcc   2580
cttattcctt tgaacctttc agttcgagct ttcccacttc atcgcagctt gactaacagc   2640
taccccgctt gagcagacat caccatgcct gaactcaccg cgacgtctgt cgagaagttt   2700
ctgatcgaaa agttcgacag cgtctccgac ctgatgcagc tctcggaggg cgaagaatct   2760
cgtgctttca gcttcgatgt aggagggcgt ggatatgtcc tgcgggtaaa tagctgcgcc   2820
gatggtttct acaaagatcg ttatgtttat cggcactttg catcggccgc gctcccgatt   2880
ccggaagtgc ttgacattgg ggaattcagc gagagcctga cctattgcat ctcccgccgt   2940
gcacagggtg tcacgttgca agacctgcct gaaaccgaac tgcccgctgt tctgcagccg   3000
gtcgcggagg ccatggatgc gatcgctgcg gccgatctta gccagacgag cgggttcggc   3060
ccattcggac cgcaaggaat cggtcaatac actacatggc gtgatttcat atgcgcgatt   3120
gctgatcccc atgtgtatca ctggcaaact gtgatggacg acaccgtcag tgcgtccgtc   3180
gcgcaggctc tcgatgagct gatgctttgg gccgaggact gccccgaagt ccggcacctc   3240
gtgcacgcgg atttcggctc caacaatgtc ctgacggaca atggccgcat aacagcggtc   3300
attgactgga gcgaggcgat gttcggggat tcccaatacg aggtcgccaa catcttcttc   3360
tggaggccgt ggttggcttg tatggagcag cagacgcgct acttcgagcg gaggcatccg   3420
gagcttgcag gatcgccgcg gctccgggcg tatatgctcc gcattggtct tgaccaactc   3480
tatcagagct tggttgacgg caatttcgat gatgcagctt gggcgcaggg tcgatgcgac   3540
gcaatcgtcc gatccggagc cgggactgtc gggcgtacac aaatcgcccg cagaagcgcg   3600
gccgtctgga ccgatggctg tgtagaagta ctcgccgata gtggaaaccg acgccccagc   3660
actcgtccga gggcaaagga atagagtaga tgccgaccgc gggatccact taacgttact   3720
gaaatcatca aacagcttga cgaatctgga tataagatcg ttggtgtcga tgtcagctcc   3780
ggagttgaga caaatggtgt tcaggatctc gataagatac gttcatttgt ccaagcagca   3840
aagagtgcct tctagtgatt taatagctcc atgtcaacaa gaataaaacg cgttttcggg   3900
tttacctctt ccagatacag ctcatctgca atgcattaat gcattgactg caacctagta   3960
acgccttnca ggctccggcg aagagaagaa tagcttagca gagctatttt cattttcggg   4020
```

-continued

```
agacgagatc aagcagatca acggtcgtca agagacctac gagactgagg aatccgctct   4080

tggctccacg cgactatata tttgtctcta attgtacttt gacatgctcc tcttctttac   4140

tctgatagct tgactatgaa aattccgtca ccagcncctg ggttcgcaaa gataattgca   4200

tgtttcttcc ttgaactctc aagcctacag gacacacatt catcgtaggt ataaacctcg   4260

aaatcanttc ctactaagat ggtatacaat agtaaccatg catggttgcc tagtgaatgc   4320

tccgtaacac ccaatacgcc ggccgaaact tttttacaac tctcctatga gtcgtttacc   4380

cagaatgcac aggtacactt gtttagaggt aatccttctt tctagtacaa gcagccagga   4440

ttcaccatcc acgacaattt cgacgaagtc tgcgcccact ggcactgtca caactaggag   4500

tcaggattta ccctcaacga ccatctctac gagatctcct gagactgaaa ctgagactgc   4560

aacaacaaaa agtcagggtt caccgtcaat tactctctct acaaggtctt cctccgctga   4620

gactgtatca acaagaagtc agcattcatc gtctacaaca atttcaacga agtctgcacc   4680

aactgagact ggtacgacaa gtgaacattc aacatcaatg cctgtctcta cgagatcggc   4740

ttccaccgag actgtaataa cgagaagtca gaattcagat tctcaatcaa tgacagtctc   4800

tacaagatcg ccttccaccg aaagtatcac aacaagaagt caaggttcgc catcagagac   4860

attttcaacc aagtctgttc cagtagatac catctcaact gaattgcctt ctcaaacgcc   4920

aacaacgatt ataacgggaa caccttctga tcctgtatca gccccgacca ccacggttcc   4980

tcccaatcct accctgacgc tcgccccatc ttcctccaca acagaagacc gcaccacaat   5040

cactactata atcaccacat cctacgtcac tgtctgtccc actggcttta ccacggtcac   5100

aataacatac accaccacct actgcccgga gaccgcttcg ctcacgccaa ctcagccccc   5160

tattccggga gctccagccc ctccaccaga tggctggaca acaattgtca ccgtgtgccc   5220

ccagtgcgcc ccaacgccaa ctaccgtcac actcacggtc cccacaagat ctgccttcct   5280

tcccgcacgc acggagactc gccctgttgt cactgtggtc ccagtgccgg agaatccaat   5340

taagaacgtg aagcctagtg agtccggaga ttttgtgact gttactacag cggcgccggc   5400

aacggttaca aagacgttgg aatacaacaa cccggtggat tccgatgtga atgtccaacc   5460

cacgggtggt agttccccccg tcgagtttga aggcagtgcg atgactgtaa gaagtatgga   5520

tgtggtcgcg aaagccctga ttaccgctgg agcgctgtgt tgggattgtt cttggggtta   5580

taatctgtta atttgctgag gcgatatata cacattttct tcggaggggt gtgtacataa   5640

tgtcacgggt gctgtacttg tacatac                                        5667
```

<210> SEQ ID NO 14
<211> LENGTH: 4849
<212> TYPE: DNA
<213> ORGANISM: Coccidioides posadasii
<220> FEATURE:
<221> NAME/KEY: misc_feature
<222> LOCATION: 3065, 3273, 3364
<223> OTHER INFORMATION: n = A,T,C or G

<400> SEQUENCE: 14

```
gtgcgctgta agaccatgat cacttcattt gatggcccta actggagacg cttcttttag     60

caccaacatg tggcactttg tacttgacat cagcaccgcg caccctgtgc tcaccggctg    120

actagtgata ctttagggca aagtggtggg gatcctggcg gttccggggc tcgtcccttg    180

cctagaaaca ttcccgcatg gtatatacgt aggaaaccgg gcaaagttgg taattacctt    240

ggttcactca atgtcatagt catctggccc ttcaacgcag gaatttcaga ccatatgtat    300

aacagctcat attgacctgg gaaactctcc aagaaatgct aacatttgag ccatttatca    360
```

-continued

```
tcatctacca tcactatcta ctgctaattg gtttccggca atttctctca gtcttacatt    420
cctcacagct ccagcatgat gaactccact ggtcaacatc aaaatgctta cccgaatttt    480
agcttgcgag ggagagtata tatcgtcact gggggcggca gggggctagg attagtgatg    540
gcagaggcaa taactgaggc aggtgcggaa ggtaaggatg atcaatttcg actgtgagtg    600
gcccttattg atgaagctaa tggccgttct agttcactgt tttgatatcc taccagaacc    660
cgatgatgaa ttcgttcgga cacaggagct cgccagcaag gcacacgtcg gcaatctgca    720
ctatcatcat gtggacgtga gagactcgaa gcatctcaac gatgttgtgg agaagatcgc    780
attgcgcagt aatcgcctag acggactagt cgcagctgct ggagtacagc aagtgaccga    840
agcaatcgac tacaccgccg acgatgtaac gaagatgctg gatataaact atactggtgt    900
ttttatgacc gctcaagcca cggctcgcca aatgatgaaa ctcggctgca atggttccat    960
agtcctggtg gctagcagtt ccaggtggaa tgttatgatg agcattgtat taaatcagga   1020
gatatagcat gatctctagt tagctcacca caaaagtcag acggcgtaac caaaagtcac   1080
acaacacaag ctgtaaggat ttcggcacgg ctacggaaga cggagaagcc accttcagtg   1140
gactcgagta ccatttaatt ctatttgtgt ttgatcgaga cctaatacag cccctacaac   1200
gaccatcaaa gtcgtatagc taccagtgag gaagtggact caaatcgact tcagcaacat   1260
ctcctggata aactttaagc ctaaactata cagaataaga taggtggaga gcttataccg   1320
agctcccaaa tctgtccaga tcatggttga ccggtgcctg gatcttccta tagaatcatc   1380
cttattcgtt gacctagctg attctggagt gacccagagg gtcatgactt gagcctaaaa   1440
tccgccgcct ccaccatttg tagaaaaatg tgacgaactc gtgagctctg tacagtgacc   1500
ggtgactctt tctggcatgc ggagagacgg acggacgcag agagaagggc tgagtaataa   1560
gccactggcc agacagctct ggcggctctg aggtgcagtg gatgattatt aatccgggac   1620
cggccgcccc tccgccccga agtggaaagg ctggtgtgcc cctcgttgac caagaatcta   1680
ttgcatcatc ggagaatatg gagcttcatc gaatcaccgg cagtaagcga aggagaatgt   1740
gaagccaggg gtgtatagcc gtcggcgaaa tagcatgcca ttaacctagg tacagaagtc   1800
caattgcttc cgatctggta aaagattcac gagatagtac cttctccgaa gtaggtagag   1860
cgagtacccg gcgcgtaagc tccctaattg gcccatccgg catctgtagg gcgtccaaat   1920
atcgtgcctc tcctgctttg cccggtgtat gaaaccggaa aggccgctca ggagctggcc   1980
agcggcgcag accgggaaca caagctggca gtcgacccat ccggtgctct gcactcgacc   2040
tgctgaggtc cctcagtccc tggtaggcag ctttgccccg tctgtccgcc cggtgtgtcg   2100
gcggggttga caaggtcgtt gcgtcagtcc aacatttgtt gccatatttt cctgctctcc   2160
ccaccagctg ctcttttctt ttctctttct tttcccatct tcagtatatt catcttccca   2220
tccaagaacc tttatttccc ctaagtaagt actttgctac atccatactc catccttccc   2280
atcccttatt cctttgaacc tttcagttcg agctttccca cttcatcgca gcttgactaa   2340
cagctacccc gcttgagcag acatcaccat ggccaagttg accagtgccg ttccggtgct   2400
caccgcgcgc gacgtcgccg gagcggtcga gttctggacc gaccggctcg ggttctcccg   2460
ggacttcgtg gaggacgact tcgccggtgt ggtccgggac gacgtgaccc tgttcatcag   2520
cgcggtccag gaccaggtgg tgccggacaa caccctggcc tgggtgtggg tgcgcggcct   2580
ggacgagctg tacgccgagt ggtcggaggt cgtgtccacg aacttccggg acgcctccgg   2640
gccggccatg accgagatcg gcgagcagcc gtgggggcgg gagttcgccc tgcgcgaccc   2700
```

-continued

```
ggccggcaac tgcgtgcact tcgtggccga ggagcaggac tgaccgacgc cgaccaacac   2760

cgccggtccg acggcggccc acgggtccca ggagcttgag atccacttaa cgttactgaa   2820

atcatcaaac agcttgacga atctggatat aagatcgttg gtgtcgatgt cagctccgga   2880

gttgagacaa atggtgttca ggatctcgat aagatacgtt catttgtcca agcagcaaag   2940

agtgccttct agtgatttaa tagctccatg tcaacaagaa taaaacgcgt tttcgggttt   3000

acctcttcca gatacagctc atctgcaatg cattaatgca ttgactgcaa cctagtaacg   3060

ccttncaggc tccggcgaag agaagaatag cttagcagag ctattttcat tttcgggaga   3120

cgagatcaag cagatcaacg gtcgtcaaga gacctacgag actgaggaat ccgctcttgg   3180

ctccacgcga ctatatattt gtctctaatt gtactttgac atgctcctct tctttactct   3240

gatagcttga ctatgaaaat tccgtcacca gcncctgggt tcgcaaagat aattgcatgt   3300

ttcttccttg aactctcaag cctacaggac acacattcat cgtaggtata aacctcgaaa   3360

tcanttccta ctaagatggt atacaatagt aaccatgcat ggttgcctag tgaatgctcc   3420

gtaacaccca atacgccggc cgaaactttt ttacaactct cctatgagtc gtttacccag   3480

aatgcacagg tacacttgtt tagaggtaat ccttctttct agagcttggc actggccgtc   3540

gttttacaac gtcgtgactg ggaaaaccct ggcgttaccc aacttaatcg ccttgcagca   3600

catccccctt tcgccagctg gcgtaatagc gaagaggccc gcaccgatcg cccttcccaa   3660

cagttgcgca gcctgaatgg cgaatggcgc ctgatgcggt attttctcct tacgcatctg   3720

tgcggtattt cacaccgcat atggtgcact ctcagtacaa tctgctctga tgccgcatag   3780

ttaagccagc cccgacaccc gccaacaccc gctgacgcgc cctgacgggc ttgtctgctc   3840

ccggcatccg cttacagaca agctgtgacc gtctccggga gctgcatgtg tcagaggttt   3900

tcaccgtcat caccgaaacg cgcgagacga aagggcctcg tgatacgcct atttttatag   3960

gttaatgtca tgataataat ggtttcttag acgtcaggtg gcacttttcg gggaaatgtg   4020

cgcggaaccc ctatttgttt atttttctaa atacattcaa atatgtatcc gctcatgaga   4080

caataaccct gataaatgct tcaataatat tacactcaac gaccattccc cagacgatcc   4140

ccggtacgtg ccgttgtggg cagagatgcg cgtaatgcag gcgagtggga ccaaggtgat   4200

ggggatggtt gggggtgccg ccaaaggcag ttatcagagg cttgatggaa gcgtggcaga   4260

ttttgaagcg ttctactgcc cgctccgtga tatgatacga acgcggaatt tgaatggcct   4320

ggacctcgac gtagaggagg atatgtccct cgacggcatt attcgcctga ttgatcgcct   4380

caaatcggat tttggagatg agtttatcat caccctagct cccgtggcca ctgctatggt   4440

gcgtggcctg agacatctct ccggctttga ttaccgagca ttggagactg ccaggggctc   4500

aaaaatatct tggtataatg tgcagttcta caatggacgg ggtcatatgc tgcatcccag   4560

cgtctacgat accatcatac atcaaggctg ggaggcggag aggatcgtta taggtctctt   4620

gaccaatccc gctaacgggt ctcagggcta tgttccaatg gaaacgataa gttcggtgtt   4680

agcaaacgtg ctgacaaagt acccatcgtt cggggggta tcagggtggg aatacttcaa   4740

cgcaatgccg gggggcatct ctcgcccatg ggaatgggcc gcttcaatct cactgatagt   4800

gggaatgaag acagtccttg cgtgtgcgac ttctgcgctt tactcgaag              4849
```

<210> SEQ ID NO 15
<211> LENGTH: 20
<212> TYPE: DNA
<213> ORGANISM: Coccidioides posadasii

<400> SEQUENCE: 15

-continued

```
ccgtcgaggg agtctgatag                                                   20


<210> SEQ ID NO 16
<211> LENGTH: 20
<212> TYPE: DNA
<213> ORGANISM: Coccidioides posadasii

<400> SEQUENCE: 16

gtatgtacaa gtacagcacc                                                   20


<210> SEQ ID NO 17
<211> LENGTH: 21
<212> TYPE: DNA
<213> ORGANISM: Coccidioides posadasii

<400> SEQUENCE: 17

gtgcgctgta agaccatgat c                                                 21


<210> SEQ ID NO 18
<211> LENGTH: 20
<212> TYPE: DNA
<213> ORGANISM: Coccidioides posadasii

<400> SEQUENCE: 18

cttcgagtaa agcgcagaag                                                   20


<210> SEQ ID NO 19
<211> LENGTH: 517
<212> TYPE: DNA
<213> ORGANISM: Coccidioides posadasii

<400> SEQUENCE: 19

aagttctcac tcctcagcgc tatcgcagcg gctgtcttcg tccctttcac atccgccact      60

ccacttgcta gcacggccga cctcagctac gacactcact acgatgaccc atccctgccc     120

ctgagtggcg tcacctgttc tgacggggac aatggcatga taacaaaggg ctacaacacc     180

gccggcgaga taccaaacta ccctcacgtc ggaggagctt ttacggtcga aacgtggaac     240

agccccaact gtggaaagtg ctacaaagtg acatacaatg ctaaaacgat ttttttgact     300

gcgatcgacc acagcaactc cggatttaat atcgcgaaga agtcgatgga cgtattgacg     360

aacggacggg cagaggaatt gggcaggatc aaggtgacct acgaagaggt cgcctcgtcg     420

ttgtgcgggt tgaaataaag gcgtattggg cgatgtgccg caatgctgag tgcgatgatt     480

tgatatttgt ttggttgaag gggaggaacc ttaatgt                              517


<210> SEQ ID NO 20
<211> LENGTH: 25
<212> TYPE: DNA
<213> ORGANISM: Coccidioides posadasii

<400> SEQUENCE: 20

aagttctcac tcctcagcgc tatcg                                             25


<210> SEQ ID NO 21
<211> LENGTH: 25
<212> TYPE: DNA
<213> ORGANISM: Coccidioides posadasii

<400> SEQUENCE: 21

acattaaggt tcctcccctt caacc                                             25
```

-continued

<210> SEQ ID NO 22
<211> LENGTH: 20
<212> TYPE: DNA
<213> ORGANISM: Coccidioides posadasii

<400> SEQUENCE: 22
acagcgtctc cgacctgatg 20

<210> SEQ ID NO 23
<211> LENGTH: 20
<212> TYPE: DNA
<213> ORGANISM: Coccidioides posadasii

<400> SEQUENCE: 23
cctcgctcca gtcaatgacc 20

<210> SEQ ID NO 24
<211> LENGTH: 21
<212> TYPE: DNA
<213> ORGANISM: Coccidioides posadasii

<400> SEQUENCE: 24
ggtgattcga gtccctgact g 21

<210> SEQ ID NO 25
<211> LENGTH: 21
<212> TYPE: DNA
<213> ORGANISM: Coccidioides posadasii

<400> SEQUENCE: 25
cagtctcagt ggaagctgac c 21

<210> SEQ ID NO 26
<211> LENGTH: 628
<212> TYPE: DNA
<213> ORGANISM: Coccidioides posadasii

<400> SEQUENCE: 26
ccttccaccg aaagtatcac aacaagaagt caaggttcgc catcagagac attttcaacc 60
aagtctgttc cagtagatac catctcaact gaattgcctt ctcaaacgcc aacaacgatt 120
ataacgggaa caccttctga tcctgtatca gccccgacca ccacggttcc tcccaatcct 180
accctgacgc tcgccccatc ttcctccaca acagaagacc gcaccacaat cactactata 240
atcaccacat cctacgtcac tgtctgtccc actggcttta ccacggtcac aataacatac 300
accaccacct actgcccgga gaccgcttcg ctcacgccaa ctcagccccc tattccggga 360
gctccagccc ctccaccaga tggctggaca acaattgtca ccgtgtgccc ccagtgcgcc 420
ccaacgccaa ctaccgtcac actcacggtc cccacaagat ctgccttcct tcccgcacgc 480
acggagactc gccctgttgt cactgtggtc ccagtgccgg agaatccaat taagaacgtg 540
aagcctagtg agtccggaga ttttgtgact gttactacag cggcgccggc aacggttaca 600
aagacgttgg aatacaacaa cccggtgg 628

<210> SEQ ID NO 27
<211> LENGTH: 20
<212> TYPE: DNA
<213> ORGANISM: Coccidioides posadasii

<400> SEQUENCE: 27
ccttccaccg aaagtatcac 20

-continued

<210> SEQ ID NO 28
<211> LENGTH: 20
<212> TYPE: DNA
<213> ORGANISM: Coccidioides posadasii

<400> SEQUENCE: 28
ccaccgggtt gttgtattcc 20

<210> SEQ ID NO 29
<211> LENGTH: 25
<212> TYPE: DNA
<213> ORGANISM: Coccidioides posadasii

<400> SEQUENCE: 29
tctgtagggc gtccaaatat cgtgc 25

<210> SEQ ID NO 30
<211> LENGTH: 23
<212> TYPE: DNA
<213> ORGANISM: Coccidioides posadasii

<400> SEQUENCE: 30
catggtgatg tctgctcaag cgg 23

<210> SEQ ID NO 31
<211> LENGTH: 19
<212> TYPE: DNA
<213> ORGANISM: Coccidioides posadasii

<400> SEQUENCE: 31
gccgcagtaa tccaactag 19

<210> SEQ ID NO 32
<211> LENGTH: 21
<212> TYPE: DNA
<213> ORGANISM: Coccidioides posadasii

<400> SEQUENCE: 32
gaattgctga cagcctatct g 21

<210> SEQ ID NO 33
<211> LENGTH: 605
<212> TYPE: DNA
<213> ORGANISM: Coccidioides posadasii

<400> SEQUENCE: 33
caccggctga ctagtgatac tttagggcaa agtggtgggg atcctggcgg ttccggggct 60
cgtcccttgc ctagaaacat tcccgcatgg tatatacgta ggaaaccggg caaagttggt 120
aattaccttg gttcactcaa tgtcatagtc atctggccct tcaacgcagg aatttcagac 180
catatgtata acagctcata ttgacctggg aaactctcca agaaatgcta acatttgagc 240
catttatcat catctaccat cactatctac tgctaattgg tttccggcaa tttctctcag 300
tcttacattc ctcacagctc cagcatgatg aactccactg gtcaacatca aaatgcttac 360
ccgaatttta gcttgcgagg gagagtatat atcgtcactg ggggcggcag ggggctagga 420
ttagtgatgg cagaggcaat aactgaggca ggtgcggaag gtaaggatga tcaatttcga 480
ctgtgagtgg cccttattga tgaagctaat ggccgttcta gttcactgtt ttgatatcct 540
accagaaccc gatgatgaat tcgttcggac acaggagctc gccagcaagg cacacgtcgg 600

-continued

```
caatc                                                              605

<210> SEQ ID NO 34
<211> LENGTH: 20
<212> TYPE: DNA
<213> ORGANISM: Coccidioides posadasii

<400> SEQUENCE: 34

caccggctga ctagtgatac                                               20

<210> SEQ ID NO 35
<211> LENGTH: 20
<212> TYPE: DNA
<213> ORGANISM: Coccidioides posadasii

<400> SEQUENCE: 35

gattgccgac gtgtgccttg                                               20

<210> SEQ ID NO 36
<211> LENGTH: 5588
<212> TYPE: DNA
<213> ORGANISM: Coccidioides posadasii

<400> SEQUENCE: 36

cttcacctga gaaaaagaaa aggggaaagg ctgcagcgga ggagaagcca aaacgtgccc     60

aacctgcagt tgctgagaca ccaaagagtg agaagaagac tcgtaagaag cgcaagagtg    120

aagctgctgc agcggagtaa atttgccaaa acctttgaga attaatcgta tcgaatgtgt    180

atgtttagca gaatggagtc tggctcactt tcgtctctgc aattttcaca atttgttcag    240

ggtttcgtct acattcgaca ttattgtttg ctctgcaatg gatcttttcg cgtgcatcaa    300

acttgagctg ctggagaaca gtccacttga caaggcaaac gctcatatgt ttcatggttg    360

tcttctttct tttttttac ttttcttttt tcttttttttt tttttttcg gggggctccc    420

acggattcat attgtacttt ctttgagcca gctttaggcc tttctgtctt atcgatattt    480

gaatgtaaaa gtggatttgt attccgaaag gccatcttga ctatatacgc ttcatcattc    540

acaccatcga gtgttgatcc gccggcaagg cccgcttcgg gtaccgggac catgcgcgag    600

atcgtgcgac tgcgaaggtg cacggtctac gaagtgcatc gttagcaaaa caccaagcca    660

cgtaacttca tgaatcaagg atcctaggct aagtttgcga gctacgggta taaccgcatg    720

gatactgtgg agctacggcg ataaggtagt atggatgggt gaccctttgc agccaacgga    780

gggcgaccat tataactagt gggttgatat ctccaaagac acgttcccgg tgggctagaa    840

tgagcaggtt gccgataaaa ttgtatccca aaggccaatg cgcatacata gatatagcca    900

ctgctgttgt gaaacatcct taccccgtct ccctatccga gatggatgta tgtacacaca    960

tacaactgga cactccttga cctagcgtaa ttgacgaaag cacagaagtc aaaaccttgc   1020

tttggcctgc tgccggaata gatgatggga ttgatgggcc tggaagttaa acccgcccaa   1080

ccaccccccgc ctgcctgcaa cttaaatctc ggactacata aagccggccc ttcggcagaa   1140

ccattttgac attaatcatt attgctctta cttccggttc gcagcgtaca gtcaagaaga   1200

gcaaggtgag tattgtggtt aaattcacag cgcattgaag ctgcccgctt ttctccgctt   1260

gataggctca ctccatcctt aactagcacg atacgccgcc aaggtggcct cagtcgacta   1320

gcaatgcagc tcgtgccgcg agaggtaggc gattcgccag ccctatgtgc cttgactcct   1380

cactgcttga atcattcagc cagttacaga tgaaattggg tggatagctc ttgtaaaaca   1440

aactcgacat gattttcttt ttctcttcct gatcgcccta ttgtctacgg agtactgtat   1500
```

-continued

```
gaggattgaa ggagtattgg tgaatccgac gctgatggct gctgcaagta gatcgataaa   1560
ctgaccatct ctaatctggg atttctggcc cagcggagat tggcccgggg agtgaggttg   1620
aatcatgcag aagcgactgt aagttgaaca aaaaagcttg gtgttcttgt catggcttgg   1680
tttttcaacg attctaacat gggtgttcta ggcgttgatc gcatccaatc tccaagaggt   1740
acgtgggggt tgcgagtcag tcagtcaagt tatgcatttt acaggccgcg tcaagccttc   1800
tttagaatgg atgtttctcg gagtagaact tccaactaac atcgcactgg cagcttattc   1860
gagatggcaa caattcggtg gcagatctca tgacgatcgg caaggagatg cttggacgtc   1920
gacatgtcct accctctgtc gtggccacct tgaaacaagt tcaagttgaa ggaacttttc   1980
ccactgggac caacctgatc accgtggtca atcccgtttg ttcggatgat ggcgacctgg   2040
agaaagccct ctacggaagc tttttgcctg tgccgccgaa agaaacgttc ccggatcctg   2100
atccggatga ctatcagcca gagaagatgc ctggcgctgt gatacccctc aaaacgagca   2160
agaaaattga gctcaatgcc gggagaaata gaattatgct taaagtgaca agtcgaggag   2220
accggcccat tcaggtgagt atgtaaagca cttctagtgg gctttcgttc ttttgaatgc   2280
tatgttgcct tgcttagctg cttccgtcga taagaattaa cgcttacagc cattaggttg   2340
gttcacacta tcattttata gaggtgaatc cacaattgga cttcgaccgt gcgaaggcgt   2400
acggatatcg ccttgacatc ccagctggga cgtctatccg ctttgaaccc ggtgctacca   2460
aggcaatccc tctcgtcgaa attggcggca agagaatcat tcgagggggc aaccacatcg   2520
ccgtcgggca agtggatttc cgaagagttg atgaaatcat catgcgtctg caaaaagctg   2580
gatttgcgta cactccggag cctaaacagg atgctcattt gatcgagcca ttttcaatga   2640
cgcgggaagc atatgctcga atgtttggtc ctaccactgg agatgtagtc aagctaggaa   2700
ccacagattt gtggattaaa gtcgaaaagg acctgaccta ctatggtgac gaatgttcat   2760
tcggtggtgg caagaccata agagacggga tggggcaagc tacaggaagg cattccgtgg   2820
atgtcctgga tacagtcctg gtgaacgcgc taattgtcga ttggacgggt atttacaagg   2880
ctgatattgg actaaaagat ggattgatct gcggaatcgg caaagctgga aacccagaca   2940
tgatggatgg tgtcaccccc aacatgatag ttggctcttc gacagatgtt atcgcatgtg   3000
aaggaaaaat tgtcactgca ggaggaattg acacacacgt ccattttata tgcccacagc   3060
aggtcgagga agccctcgcc tccggagtca cgactcttct cggtggcggc accggtccaa   3120
ctgagggatc aaatgcgact acatgcacac cggctccaaa tcagttcaag acgatgatgc   3180
aggcttgtga tcatcttcca ataaacgttg gccttacagg caaaggtaat gacagcggtc   3240
ttccatctct gagggatcaa tgccgtgcag gagccgctgg cttgaaggtg catgaagatt   3300
ggggtgcaac gccggctgtc attgatacat gcctccaggt ctgcgacgag ttcgatattc   3360
aatgtctcat ccataccgac accctgaacg aatctggctt cgttgaacag accatcaatg   3420
cctttaaaaa tcgagtgatt catacgtacc acactgaggg tgctggagga ggccacgctc   3480
cagatatcat atccgtcgtc gagaagccaa acgtcctgcc cagcagtacg aatcccactc   3540
gtccgtatac ggtaaatact ttagatgaac atctggacat ggtaatggtc tgccatcatt   3600
tgtccaaaga tattcctgaa gacgtggctt ttgcggaaag ccggatccga tccgagacaa   3660
ttgctgcaga agacgttctt catgacacgg gagccatcag catgctatcc tcggactctc   3720
aagctatggg acgctgtgga gaagttgttg ttcggacatg gaacactgca cataagaata   3780
aaatggaacg agggcgactc aaggaagatg aagggacgga ttctgataat tttagggtta   3840
```

-continued

```
aacggtatat cagcaagtac accatcaacc ctgccattgc acaggggatg gcccacacta   3900
ttgggagcgt ggaagttggc aagaccgctg atttggttct gtggaaattt gccaactttg   3960
ggactaaacc gagtatggtc ttgaagtctg gaatggctgt ctcagcgcag atggtatgat   4020
cgcctctata ccacttattt tggtaccagc attcgaagga gaggaatgtg ctgacataga   4080
gatgtccagg gtgatcccaa tggctctatc cccacaatcg agcctattat tatgaggcct   4140
atgtacgctg taagtggaat gctcatcgta atccatctga tttggacgac gagttaacta   4200
gattccctct tttctaagag tcttaaccct aaagcctcaa tcatgttcgt atcccaagca   4260
tccatcaagc ttggtatcat cgacagttac cacctgaaga agcggatcga gccagtgaag   4320
aattgtcgga atataagcaa gagagatatg aaatttaatg atattatgcc caaaatgaga   4380
gtcgatccgg agagctatgt aagtgtcata tatgttcttt atgttccacc tttctaaaga   4440
cacctttgtt gtaagcgctg actgtcgtat tgcctaggtt gtcgaggctg acggggaaga   4500
gtgcaccgct gagccagtgt cagagttgcc tttaacacaa gattatttcg tttactgaaa   4560
attggtggag accatagaac gtctccacag attagtcgtg gaaaagtaat gctcatggcg   4620
atagtatcct tctgtacctg ttttgatgaa tattagtaca ttttattgca tatctattct   4680
cttggtcctg tgcgcctcca cgtgagcatc cttttttgct aatccccaac gccctacaga   4740
gatggaccat tgagttatct gaaattctaa attcgcaata agctctccca gaaaaacagt   4800
aagataacgc gcccggaact ccttgctcca aaaaaaaaaa aaaaaaaaag ggaatacaac   4860
tattcaaagc tcttcatcca tcacagtatg attattgcct gccgaaatga gcgagtagag   4920
agtcgaccac gtctcgtgct tggccgcacg atacgcagag atccttgaat gcatacgtct   4980
tagcattgac gccttgcggt cctgacaact aggtgggagg gttgtggctt ggtccggatc   5040
gttttcgttg tctttgttat cgtcatctga ggccatttca ataatgtctt gaggatcaaa   5100
tgctgatggc gagattgata ggggggtgct gggaggatag ttatctccgg tgtcttcata   5160
gtcggataag agttgaagct gtgtgtcggg gtctgatgca gcatgctcta gattctcttc   5220
ggggattgcg aaggaggaat gctggaggtt tgaactagca tattgtggcg agaatagtcc   5280
ttgtggctgc gattgagcct gcgagtccgt gaacgatgat tcgaggaaaa aatcaatttc   5340
gttactaagg gccttttgtt ccaaagcctg tctgatagct tggattctga tgccacgcga   5400
cgttgacaac tcgtctggct gtgatagaga aagattactt gtgatttgtg atgggaaaga   5460
gaatgacaag tccgtgtcgg ctgtcgcaaa atccaaatgc tcagcaggct gtccttttcc   5520
gggttgtgaa ttttgccctt ctgaatctga actgagaaca atcacgggat actcaagtgc   5580
ttgtggag                                                            5588

<210> SEQ ID NO 37
<211> LENGTH: 836
<212> TYPE: PRT
<213> ORGANISM: Coccidioides posadasii

<400> SEQUENCE: 37

Met Gln Leu Val Pro Arg Glu Ile Asp Lys Leu Thr Ile Ser Asn Leu
1               5                   10                  15

Gly Phe Leu Ala Gln Arg Arg Leu Ala Arg Gly Val Arg Leu Asn His
            20                  25                  30

Ala Glu Ala Thr Ala Leu Ile Ala Ser Asn Leu Gln Leu Ile Arg Asp
        35                  40                  45

Gly Asn Asn Ser Val Ala Asp Leu Met Thr Ile Gly Lys Glu Met Leu
    50                  55                  60
```

-continued

```
Gly Arg Arg His Val Leu Pro Ser Val Val Ala Thr Leu Lys Gln Val
65                  70                  75                  80

Gln Val Glu Gly Thr Phe Pro Thr Gly Thr Asn Leu Ile Thr Val Val
                85                  90                  95

Asn Pro Val Cys Ser Asp Asp Gly Asp Leu Glu Lys Ala Leu Tyr Gly
            100                 105                 110

Ser Phe Leu Pro Val Pro Pro Lys Glu Thr Phe Pro Asp Pro Asp Pro
        115                 120                 125

Asp Asp Tyr Gln Pro Glu Lys Met Pro Gly Ala Val Ile Pro Leu Lys
    130                 135                 140

Thr Ser Lys Lys Ile Glu Leu Asn Ala Gly Arg Asn Arg Ile Met Leu
145                 150                 155                 160

Lys Val Thr Ser Arg Gly Asp Arg Pro Ile Gln Val Gly Ser His Tyr
                165                 170                 175

His Phe Ile Glu Val Asn Pro Gln Leu Asp Phe Asp Arg Ala Lys Ala
            180                 185                 190

Tyr Gly Tyr Arg Leu Asp Ile Pro Ala Gly Thr Ser Ile Arg Phe Glu
        195                 200                 205

Pro Gly Ala Thr Lys Ala Ile Pro Leu Val Glu Ile Gly Gly Lys Arg
    210                 215                 220

Ile Ile Arg Gly Gly Asn His Ile Ala Val Gly Gln Val Asp Phe Arg
225                 230                 235                 240

Arg Val Asp Glu Ile Ile Met Arg Leu Gln Lys Ala Gly Phe Ala Tyr
                245                 250                 255

Thr Pro Glu Pro Lys Gln Asp Ala His Leu Ile Glu Pro Phe Ser Met
            260                 265                 270

Thr Arg Glu Ala Tyr Ala Arg Met Phe Gly Pro Thr Thr Gly Asp Val
        275                 280                 285

Val Lys Leu Gly Thr Thr Asp Leu Trp Ile Lys Val Glu Lys Asp Leu
    290                 295                 300

Thr Tyr Tyr Gly Asp Glu Cys Ser Phe Gly Gly Gly Lys Thr Ile Arg
305                 310                 315                 320

Asp Gly Met Gly Gln Ala Thr Gly Arg His Ser Val Asp Val Leu Asp
                325                 330                 335

Thr Val Leu Val Asn Ala Leu Ile Val Asp Trp Thr Gly Ile Tyr Lys
            340                 345                 350

Ala Asp Ile Gly Leu Lys Asp Gly Leu Ile Cys Gly Ile Gly Lys Ala
        355                 360                 365

Gly Asn Pro Asp Met Met Asp Gly Val Thr Pro Asn Met Ile Val Gly
    370                 375                 380

Ser Ser Thr Asp Val Ile Ala Cys Glu Gly Lys Ile Val Thr Ala Gly
385                 390                 395                 400

Gly Ile Asp Thr His Val His Phe Ile Cys Pro Gln Gln Val Glu Glu
                405                 410                 415

Ala Leu Ala Ser Gly Val Thr Thr Leu Leu Gly Gly Gly Thr Gly Pro
            420                 425                 430

Thr Glu Gly Ser Asn Ala Thr Thr Cys Thr Pro Ala Pro Asn Gln Phe
        435                 440                 445

Lys Thr Met Met Gln Ala Cys Asp His Leu Pro Ile Asn Val Gly Leu
    450                 455                 460

Thr Gly Lys Gly Asn Asp Ser Gly Leu Pro Ser Leu Arg Asp Gln Cys
465                 470                 475                 480
```

-continued

```
Arg Ala Gly Ala Ala Gly Leu Lys Val His Glu Asp Trp Gly Ala Thr
                485                 490                 495

Pro Ala Val Ile Asp Thr Cys Leu Gln Val Cys Asp Glu Phe Asp Ile
            500                 505                 510

Gln Cys Leu Ile His Thr Asp Thr Leu Asn Glu Ser Gly Phe Val Glu
        515                 520                 525

Gln Thr Ile Asn Ala Phe Lys Asn Arg Val Ile His Thr Tyr His Thr
    530                 535                 540

Glu Gly Ala Gly Gly Gly His Ala Pro Asp Ile Ile Ser Val Val Glu
545                 550                 555                 560

Lys Pro Asn Val Leu Pro Ser Ser Thr Asn Pro Thr Arg Pro Tyr Thr
                565                 570                 575

Val Asn Thr Leu Asp Glu His Leu Asp Met Val Met Val Cys His His
            580                 585                 590

Leu Ser Lys Asp Ile Pro Glu Asp Val Ala Phe Ala Glu Ser Arg Ile
        595                 600                 605

Arg Ser Glu Thr Ile Ala Ala Glu Asp Val Leu His Asp Thr Gly Ala
    610                 615                 620

Ile Ser Met Leu Ser Ser Asp Ser Gln Ala Met Gly Arg Cys Gly Glu
625                 630                 635                 640

Val Val Val Arg Thr Trp Asn Thr Ala His Lys Asn Lys Met Glu Arg
                645                 650                 655

Gly Arg Leu Lys Glu Asp Glu Gly Thr Asp Ser Asp Asn Phe Arg Val
            660                 665                 670

Lys Arg Tyr Ile Ser Lys Tyr Thr Ile Asn Pro Ala Ile Ala Gln Gly
        675                 680                 685

Met Ala His Thr Ile Gly Ser Val Glu Val Gly Lys Thr Ala Asp Leu
    690                 695                 700

Val Leu Trp Lys Phe Ala Asn Phe Gly Thr Lys Pro Ser Met Val Leu
705                 710                 715                 720

Lys Ser Gly Met Ala Val Ser Ala Gln Met Gly Asp Pro Asn Gly Ser
                725                 730                 735

Ile Pro Thr Ile Glu Pro Ile Ile Met Arg Pro Met Tyr Ala Ser Leu
            740                 745                 750

Asn Pro Lys Ala Ser Ile Met Phe Val Ser Gln Ala Ser Ile Lys Leu
        755                 760                 765

Gly Ile Ile Asp Ser Tyr His Leu Lys Lys Arg Ile Glu Pro Val Lys
    770                 775                 780

Asn Cys Arg Asn Ile Ser Lys Arg Asp Met Lys Phe Asn Asp Ile Met
785                 790                 795                 800

Pro Lys Met Arg Val Asp Pro Glu Ser Tyr Val Val Glu Ala Asp Gly
                805                 810                 815

Glu Glu Cys Thr Ala Glu Pro Val Ser Glu Leu Pro Leu Thr Gln Asp
            820                 825                 830

Tyr Phe Val Tyr
        835
```

US 7,332,324 B2

ATTENUATED VACCINE USEFUL FOR IMMUNIZATIONS AGAINST *COCCIDIOIDES* SPP. INFECTIONS

RELATED APPLICATION

This application claims benefit of priority under 35 U.S.C. 119(b) of Provisional application 60/633,399, filed Dec. 3, 2004 (now abandoned), the contents of which are incorporated herein by reference.

STATEMENT REGARDING FEDERALLY FUNDED PROJECT

The United States Government owns rights in the present invention pursuant to Public Service Grants "Immunoreactive Macromolecules of *Coccidioides* Cell Types" (Al19149) and "Isolation and Expression of *Coccidioides* T-cell Antigens" (Al37232) from the National Institutes of Allergy and Infectious Diseases, National Institutes of Health.

FIELD OF THE INVENTION

The present invention relates generally to the fields of pathogenic fungi and immunology. In particular, the invention provides compositions of *Coccidioides* spp. strains attenuated by the selective targeting and replacement of genes encoding proteins necessary for the formation, maturation and replication of parasitic phase propagules. More particularly, the present invention provides compositions of *Coccidioides* spp. recombinant strains, which are useful for generating an immunological response in an individual and in vaccines and therapeutic applications of infections due to pathogenic *Coccidioides* spp. fungi, such as *C. posadasii* or *C. immitis*.

BACKGROUND OF THE INVENTION

Coccidioidomycosis, otherwise known as the San Joaquin Valley Fever, is a fungal respiratory disease of humans and wild and domestic animals, which is endemic to southwestern United States, northern Mexico, and numerous semiarid areas of Central and South America (Pappagianis, D. Epidemiology of Coccidioidomycosis. Current Topics in Medical Mycology. 1988. 2:199-23). Infection occurs by inhalation of airborne spores (arthroconidia) produced by the saprobic phase of *Coccidioides* spp., which grows in alkaline desert soil, followed by morphogenic conversion of the fungus to the virulent, parasitic phase in the host mammal.

*Coccidioides immitis* was the first described species, and is now becoming known as the Californian species. The *C. posadasii* species was recently defined, and was previously recognized as the non-Californian population of *C. immitis* (Fisher, M. C., Koenig, G. L., White, T. J., Taylor, J. W. Molecular and phenotypic description of *Coccidioides posadasii* sp. nov., previously recognized as the non-California population of *Coccidioides immitis*. Mycologia 2002. 94(1): 73-84, 2002). The differences in the two species are slight.

It is estimated that 100,000 new cases of this disease occur annually within the rapidly growing population of people who live in regions of the United States between southwest Texas and southern California, where the disease is endemic (Galgiani, J. N. Coccidioidomycosis: A regional disease of national importance; rethinking our approaches to its control. Annals of Internal Medicine. 1999. 130:293-300). Although the majority of immunocompetent individuals are able to resolve their *Coccidioides* spp. infection spontaneously, the level of morbidity associated even with the primary form of this respiratory mycosis warrants consideration of a vaccine against the disease. Immunocompromised patients, including those infected with human immunodeficiency virus, are at high risk to contract disseminated coccidioidomycosis (Ampel, N. M., C. L. Dols, and J. N. Galgiani. Results of a prospective study in a coccidioidal endemic area. American Journal of Medicine. 1993. 94:235-240). It is also apparent from results of several clinical studies that African-Americans and Asians are genetically predisposed to development of the potentially fatal, disseminated form of the respiratory disease (Galgiani, J. N. 1993. Coccidioidomycosis. Western Journal of Medicine 159:153-171).

Chitin, a linear polymer of N-acetylglucosamine, is one of the major structural components of the fungal cell wall, and is required for cell shape and morphogenesis. The enzyme chitinase hydrolyzes the 1,4-beta-linkages of N-acetyl-D-glucosamine polymers of chitin, and has been shown to play an important role in molding and shaping the cell wall of many fungi during growth and reproduction (Kuranda, M. J. & Robbins, P. W. 1991. Chitinase is required for cell separation during growth of *Saccharomyces cerevisiae*. Journal of Biological Chemistry 266, 19758-19767; Takaya, N., Yamazaki, D., Horiuchi, H., Ohta, A. & Takagi, M. 1998. Cloning and characterization of a chitinase-encoding gene (chiA) from *Aspergillus nidulans*, disruption of which decreases germination frequency and hyphal growth. Bioscience, Biotechnology, and Biochemistry 62, 60-65). In *Coccidioides* spp., the literature has reported two chitinase (CTS) genes (Pishko, E J; Kirkland, T N; Cole, G T 1995. Isolation and characterization of two chitinase-encoding genes (cts1, cts2) from the fungus *Coccidioides immitis*. Gene 167:173-7; Cole G T, Hung C Y. 2001. The parasitic cell wall of *Coccidioides immitis*. Medical Mycology 39 Supplement 1:31-40), and an additional five have been identified by us. These chitinases were grouped into two classes, bacterial-like and fungal-like, according to phylogenic analysis with other reported chitinases. Although evidence suggests that chitinases associate with the segmentation apparatus of parasitic phase *Coccidioides* spp., the specific role or function of the individual chitinases is not understood. Indeed, deletion of the CTS1 gene (a bacterial-like chitinase) from a strain of *Coccidioides posadasii* led to no discernible effects on reproductive endosporulation or virulence (Reichard, U., C. -Y. Hung, P. W. Thomas, and G. T. Cole. 2000. Disruption of the gene which encodes a serodiagnostic antigen and chitinase of the human fungal pathogen *Coccidioides immitis*. Infection and Immunity 68:5830-5838). However, fungal-like chitinases (CTS2, CTS3, and CTS4) of *Coccidioides* are more likely involved in morphogenesis based on reported data as referenced above (Kuranda & Robbins. 1991, Takaya et. al. 1998).

The rationale for commitment of research efforts to develop a *Coccidioides* spp. vaccine is based on clinical evidence that individuals who recover from the respiratory coccidioidomycosis disease retain effective long-term cellular immunity against future infections by the pathogen (Smith, C. E. 1940. American Journal of Public Health 30:600-611). In addition, early preclinical studies demonstrated that a formalin-killed whole-cell (spherule) vaccine prevented deaths in mice after infection with even very large numbers of coccidioidal spores (Levine et al. 1961. Journal of Immunology 87:218-227). However, when a similar vaccine preparation was evaluated in a human trial, there was substantial local inflammation, pain, and induration at the injection site, rendering the vaccine unacceptable (Pappagianis et al. Evaluation of the protective efficacy of the killed *Coccidioides immitis* spherule vaccine in humans. American Review of Respiratory Diseases. 1993.148:656-660). Further, there was no difference in the number of cases of coccidioidomycosis or the severity of the disease in the formalin-killed spherule vaccinated group compared to the placebo group. Therefore, the original human vaccine trial was not successful.

Other attempts to identify a suitable vaccine have focused on the creation of attenuated, live strains of *C. immitis* for the induction of an immune response. In two such attempts, investigators induced auxotrophic mutations in strains of *C. immitis* via X-ray irradiation (Foley, J. M, Berman, R. J., and Smith, C. E. X-ray irradiation of *Coccidioides immitis* arthrospores: survival curves and avirulent mutants isolated. Journal of Bacteriology. 1960. 79:480) or UV-irradiation and chemical mutagenesis (Walch, H. A. and Walch. R. K. Studies with induced mutants of *Coccidioides immitis.* In L. Ajello (ed.) Proceedings of the Second Symposium on Coccidioidomycosis. University of Arizona Press. 1960. p 339), and then utilized the attenuated strains as vaccines prior to challenging the animals with wild-type *C. immitis.* However, these and subsequent reports utilizing these strains (Pappagianis, D., Levine, H. B., Smith, C. E., Berman, R. J. and Kobayashi, G. S. Immunization of mice with viable *Coccidioides immitis.* Journal of Immunology. 1961. 86:28; Walch, H. A. and Walch. R. K. Immunization of mice with induced mutants of *Coccidioides immitis.* I. Characterization of mutants and preliminary studies of their use as viable vaccines. Sabouraudia. 1971. 9:173) demonstrated that although varying degrees of immunization were attained with these strains, the attenuated strains nevertheless were capable of converting to the parasitic phase and resulted in localized or disseminated lesions in the experimental animals. In one instance, the attenuated strain regained its virulence through the loss of the auxotrophic state, causing disease in vaccinated animals. Given the evidence of localized or disseminated disease, the investigators found the attenuated strains to be inappropriate as vaccines.

Therefore, there is a long felt need for more effective, safe and usable compositions for inducing an immune response to prevent, treat, or ameliorate infection of *Coccidioides* spp. and disease states associated with the infection.

SUMMARY OF THE INVENTION

Accordingly, it is an object herein to provide the methods for creating attenuated strains of *Coccidioides* spp. that have an immunostimulatory activity. As used herein, the term "attenuated" is used in the broadest sense to mean to render a fungus strain made less virulent or less capable of causing coccidioidomycosis in a mammal through human intervention or act. As used herein, the terms "virulent" and "virulence" means the potential to cause progressive or lethal coccidioidomycosis disease in a mammal. It is understood by those skilled in the art that such attenuated strains may be capable of growth under artificial in vitro conditions, or may be capable of limited growth when introduced into a mammal, but are of insufficient virulence to cause disease. Examples of an attenuated fungus can be found in U.S. Pat. No. 6,248,322, which by reference is incorporated herein in its entirety. Such immunostimulatory attenuated strains will be useful in the prevention and treatment of infections due to *Coccidioides* spp. In one embodiment, the attenuated *Coccidioides* spp. fungus is *Coccidioides posadasii.* In another embodiment, the attenuated *Coccidioides* spp. fungus is *Coccidioides immitis.*

In order to meet these needs, compositions and methods for the production of attenuated strains of *Coccidioides* spp. have been devised that render the strains incapable of reproducing in the parasitic, spherule-endospore phase of the fungus. Thus, such strains are replication competent, meaning that they have the ability to grow and reproduce as mycelia in the saprophytic, non-parasitic phase, but they are incapable of producing progeny endospores in the virulent parasitic phase. Such strains are otherwise intact, but their inability to reproduce in the parasitic phase results in the strain's inability to cause disease and, hence, lack of virulence.

Further, we have found that the selective introduction of genetic alterations in certain genes, leading to the disruption of the genes and corresponding loss of functional proteins encoded by those genes, results in the loss of reproductive potential in the parasitic phase of *Coccidioides* spp. fungus.

In one example, strains of recombinant *Coccidioides posadasii* fungus have been modified to render them incapable of expressing functional Cts2 and Cts3 proteins as well as a putative D-arabinitol 2-dehydrogenase (Ard1), whose coding gene (ARD1) is located immediately upstream (5') to the CTS3 gene (SEQ ID NO:6). The Cts proteins are two of several homologs of chitinase found in *Coccidioides* spp. that regulate the degredation of chitin; a key structural component of the cell wall of the fungus. As used herein, homolog means a second gene within the same species derived from a common ancestral gene that has evolved a new, though similar function.

The ⊿cts2⊿ard1⊿cts3 triple mutant strains described herein are capable of growing and reproducing in the saprobic, mycelial phase and converting to the parasitic spherule phase, but are incapable of undergoing endosporulation and, therefore, cannot replicate in the parasitic form, rendering the recombinant fungus incapable of causing disease. Hence, such strains are attenuated.

Surprisingly, we have found that such strains of attenuated fungus are capable of inducing a potent immune response. Accordingly, another aspect of the invention provides a method for inducing an immune response in a mammal sufficient to resist infection by *Coccidioides* spp., accomplished by administration to the mammal the attenuated fungus of the invention by single or multiple injections. Preferably, the administration of the attenuated fungus is by subcutaneous or intramuscular injection or intranasal instillation. In one embodiment, the recombinant fungus compositions and the methods for their administration provide protection against *Coccidioides posadasii* and or *Coccidioides immitis* infections in a mammal, such as a human. In another embodiment, the recombinant fungus compositions and the methods for their administration provide protection against *Coccidioides* spp. infection in domestic animals, including but not limited to dogs, cats, horses, and cattle.

According to preferred embodiments, compositions and methods are provided herein for the production of a cts2/ard1/cts3 null mutant comprising a transformed strain of *Coccidioides* spp. created by a targeted replacement of polynucleotides from genomic CTS 2 and ARD1/CTS3 sequences with the recombinant sequence comprising but not limited to nucleotides of SEQ ID NO:4 and nucleotides of SEQ ID NO:11. In one embodiment, the targeted replacement results in a transformed strain of *Coccidioides* spp.

with the cts2/ard1/cts3 null mutant comprising but not limited to the nucleotide sequences of SEQ ID NO:13 and SEQ ID NO:14.

In another embodiment, the attenuated fungus is incapable of producing functional CTS2, CTS3 and ARD1-encoded proteins by methods including but not limited to disruption or deletion of the genes or partial sequences of the genes encoding the proteins, by introduction of nonsense mutations in the genes, by the deletion or mutation of the promoters or terminators of said genes, or other methods known in the art. *Coccidioides posadasii* is a haploid fungus and methods for gene manipulation of this fungus are well-established (Reichard, U., et al., 2000. Infection and Immunity 68:5830-5838; Hung et al., 2002. A parasitic phase-specific adhesin of *Coccidioides immitis* contributes to the virulence of this respiratory fungal pathogen. Infection and Immunity 70:3442-3456). By such methods, deletion of the promoter of the targeted gene prevents the transcription of the desired mRNA, and deletion of terminator results in instability of the transcribed mRNA. In either case, mutants are unable to express the desired protein since there are no matured mRNA transcripts to be used as templates for translation into proteins. Deletion of partial sequences may result in expression of truncated proteins. However these proteins may not retain their biological function due to deletion of functional domains or lack of proper folding. Site-directed mutagenesis can also be used to change critical amino acids of a protein to block or attenuate their functionality.

Accordingly, in a further embodiment, the attenuated fungus is incapable of transcribing the CTS2, CTS3 and/or ARD1 genes and/or translating the resulting transcripts into polypeptides.

In yet a further embodiment, compositions and methods for the production of transformed strains of *Coccidioides* spp. in which a null mutation of the URE gene is introduced into the cts2/ard1/cts3 null mutant strains, resulting in a functional disruption of the URE gene product are provided. As the URE gene product is produced during endosporulation of the parasitic phase *Coccidioides* spp. fungus and is regarded as a virulence factor in infections due to this fungus (Mirbod, F., and R. A. Schaller. 2002. Purification and characterization of urease isolated from the pathogenic fungus *Coccidioides immitis*. Medical Mycology 40:35-44; Yu, J. -J., S. L. Smithson, P. W. Thomas, T. N. Kirkland, and G. T. Cole. 1997. Isolation and characterization of the urease gene (URE) from the pathogenic fungus *Coccidioides immitis*. Gene 198:387-391), the introduction of a Δure mutation into a cts2/ard1/cts3 null mutant strain would provide an additional margin of safety, should the latter strain undergo a reversion and regain the ability to endosporulate and reproduce. As cts2/ard1/cts3/ure null strains of *Coccidioides* spp. fungus would retain the ability to elicit an effective immune response, but would have an enhanced degree of safety. Such strains would provide safe and effective compositions useful for the prevention of infections due to *Coccidioides* spp.

A further embodiment provides the use of the recombinant attenuated strains in combination with one or more other *Coccidioides* spp. polypeptides to elicit an immune response sufficient to provide an effective immunization against *Coccidioides* spp. infection. In one embodiment the recombinant fungus and polypeptides are provided as a composition containing a mixture of said fungus and polypeptides. In another embodiment the composition is provided as separate compositions to be administered concurrently or consecutively; the latter consistent with the well-known practice of "prime-boost" for eliciting an immune response.

In one embodiment, methods for the production of *Coccidioides* spp. attenuated strains and compositions of recombinant fungal strains identical or substantially identical to the recombinant strains containing the polynucleotide sequences of SEQ ID NO:13 and SEQ ID NO:14 useful in pharmaceutical compositions are described herein.

The present invention also provides formulations of attenuated *Coccidioides* spp. fungus suitable for immunizing a mammal and methods of preparing the formulations containing the attenuated fungus. Preferred embodiments would include formulations containing adjuvants and or pharmaceutical excipients and carriers, as well as kits containing the formulated attenuated *Coccidioides* spp. fungus, to facilitate the use of the fungus for eliciting an effective immune response in a mammal.

The present invention further provides an attenuated *Coccidioides* spp. fungus incapable of endosporulation wherein the fungus is incapable of replication in the parasitic phase.

In one embodiment, the fungus is a recombinant *Coccidioides* spp. fungus incapable of producing functional endosporulation proteins; hence the fungus is incapable of replication in the parasitic phase. In a further embodiment, the recombinant *Coccidioides* fungus includes one or more mutations in the genes encoding the endosporulation proteins. For example, such mutations would include one or more deletions in the polynucleotide sequence of the genes. In a specific embodiment, the endosporulation genes include one or more CTS genes with one or more mutations. In one format, the recombinant fungus includes a CTS2 gene and a CTS3 gene wherein the genes each comprise a deletion wherein the recombinant fungus is incapable of expressing polypeptide gene products of the CTS2 and said CTS3 genes.

In another embodiment, the mutated endosporulation genes include one or more CTS genes and an ARD1 gene with one or more mutations. In a specific embodiment, the recombinant fungus includes a CTS2 gene, a CTS3 gene, and an ARD1 gene wherein a deletion in each gene renders the recombinant fungus incapable of expressing the polypeptide gene products of the CTS2, CTS3, and ARD1 genes. In one embodiment, the recombinant *Coccidioides* spp. fungus is incapable of expressing a polypeptide comprising the sequence of SEQ ID NO:3 and the sequence of SEQ ID NO:8. In a further embodiment, the recombinant *Coccidioides* spp. fungus is incapable of expressing polypeptides including the sequence of SEQ ID NO:3, the sequence of SEQ ID NO:8 and the sequence of SEQ ID NO:10.

In a further variation, the recombinant *Coccidioides* spp. fungus includes recombinant CTS2, CTS3 and ARD1 genes wherein the polynucleotide sequence of the recombinant CTS2 gene includes SEQ ID NO:13, the polynucleotide sequence of the recombinant CTS3 gene includes SEQ ID NO:14 and the polynucleotide sequence of the recombinant ADR1 gene includes SEQ ID NO:14.

In another embodiment, the recombinant *Coccidioides* fungus attenuated by loss of functional endosporulation proteins further includes mutations of one or more genes encoding additional virulence factors. In one such embodiment the virulence factor includes the URE gene wherein the mutated fungus is incapable of expressing URE-encoded protein.

In the embodiments described herein, the *Coccidioides* spp. fungus is alternatively *Coccidioides posadasii* or *Coccidioides immitis.*

The present invention provides compositions of isolated nucleic acids. In one embodiment, the isolated nucleic acid includes the sequences of SEQ ID NO:13 or SEQ ID NO:14.

Methods of eliciting an immune response in a mammal are also provided, including the step of administering to the mammal a composition including a recombinant fungus of the described embodiments in an amount sufficient to elicit an immune response. In one embodiment, the mammal is a human. In another embodiment, mammal is a domestic animal selected from the group consisting of dog, cat, horse, and bovine.

In variations of the methods for eliciting an immune response, the recombinant fungus is administered to the mammal by subcutaneous injection or by intramuscular injection.

These and other aspects of the invention will become readily apparent to those of skill in the art from the following detailed description and examples, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

BRIEF DESCRIPTION OF THE SEQUENCE LISTING

SEQ ID NO:1 depicts the nucleotide sequence of CTS2 gene;

SEQ ID NO:2 depicts the determined nucleotide sequence of CTS2 open reading frame (ORF) and stop codon;

SEQ ID NO:3 depicts the derived amino acid sequence of the native Cts2 polypeptide encoded by the nucleotide sequence of SEQ ID NO:2;

SEQ ID NO:4 depicts the nucleotide sequence of the 6891-bp ApaI/DraI, linear fragment of pΔcts2 comprising 63 bp of pCR2.1-TOPO (nt 1-63), 828-bp CTS2 fragment (nt 64-891), 3597-bp pAN7-1 fragment (nt 892-4488), 1242-bp CTS2 fragment (nt 4489-5730), and 1161-bp pCR2.1-TOPO (nt 5731-6891), used in the transformation of wild type *C. posadasii* protoplast to generate Δcts2 mutant;

SEQ ID NO:5 depicts the nucleotide sequence of the 967-bp fragment of CTS2 (corresponding to nt 829-1795 of SEQ ID NO:1), deleted from the Δcts2- and Δcts2Δard1Δcts3 mutant genome;

SEQ ID NO:6 depicts the nucleotide sequence of ARD1/CTS3 gene;

SEQ ID NO:7 depicts the determined nucleotide sequence of CTS3 open reading frame (ORF) and stop codon;

SEQ ID NO:8 depicts the derived amino acid sequence of the native Cts3 polypeptide encoded by the nucleotide sequence of SEQ ID NO:7;

SEQ ID NO:9 depicts the determined nucleotide sequence of ARD1 open reading frame (ORF) and stop codon;

SEQ ID NO:10 depicts the derived amino acid sequence of the native Ard1 polypeptide encoded by the nucleotide sequence of SEQ ID NO:9;

SEQ ID NO:11 depicts the nucleotide sequence of the 4967-bp ApaI/KpnI, linear fragment of pΔard1cts3 comprising 63 bp of pCR2.1-TOPO (nt 1-63), 971-bp ARD1/CTS3 fragment (nt 64-1034), 3137-bp pAN8 fragment (nt 1035-4171), 741-bp ARD1/CTS3 fragment (nt 4172-4912), and 55-bp pCR2.1-TOPO (nt 4913-4967), used in the transformation of Δcts2 *C. posadasii* mutant to generate the Δcts2Δard1Δcts3 triple mutant;

SEQ ID NO:12 depicts the nucleotide sequence of the 1224-bp fragment of ARD1/CTS3 (corresponding to nt 972-2195 of SEQ ID NO:6), deleted from the Δcts2Δard1Δcts3 mutant genome;

SEQ ID NO:13 depicts the nucleotide sequence of recombinant cts2 gene in the Δcts2Δard1Δcts3 mutant of *C. posadasii* (nt 1 to 828 is the CTS2 left-flank crossover region; nt 829 to 4421 is an introduced hygromycin B phosphotransferase gene [pAN7-1 plasmid fragment], and nt 4422 to 5667 is the CTS2 right-flank crossover region);

SEQ ID NO:14 depicts the nucleotide sequence of recombinant ard1/cts3 gene in the Δcts2Δard1Δcts3 mutant of *C. posadasii* (nt1 to 971 is the left-flank crossover region of ARD1; nt 972 to 4108 is an introduced phleomycin binding protein gene [pAN8-1 plasmid fragment]; and nt 4109 to 4849 is the right-flank crossover region of the CTS3 gene);

SEQ ID NO:15 depicts the forward primer used for the PCR amplification of wild type CTS2 gene (SEQ.ID-1 nt 1-3041);

SEQ ID NO:16 depicts the reverse primer used for the PCR amplification of wild type CTS2 gene (SEQ.ID-1 nt 1-3041);

SEQ ID NO:17 depicts the forward primer used for the PCR amplification of wild type ARD1/CTS3 gene (SEQ.ID-6 nt 1-2936);

SEQ ID NO:18 depicts the reverse primer used for the PCR amplification of wild type ARD1/CTS3 gene (SEQ.ID-6 nt 1-2936);

SEQ ID NO:19 depicts the nucleotide sequence of the 517-bp CSA fragment, which was amplified by PCR and used to confirm the identity of *C. posadasii* transformants;

SEQ ID NO:20 depicts the nucleotide sequence of the forward primer used in the PCR amplification of the sequence of SEQ ID NO:19;

SEQ ID NO:21 depicts the nucleotide sequence of the reverse primer used in the PCR amplification of the sequence of SEQ ID NO:19;

SEQ ID NO:22 depicts the nucleotide sequence of the forward primer derived from the HPH gene of pAN7-1, and used for PCR confirmation of integration of pΔcts2 in Δcts2 genome;

SEQ ID NO:23 depicts the nucleotide sequence of the reverse primer derived from the HPH gene of pAN7-1, and used for PCR confirmation of integration of pΔcts2 in Δcts2 genome;

SEQ ID NO:24 depicts the nucleotide sequence of the forward primer derived from the deleted fragment of CTS2, and used for PCR confirmation of deletion of CTS2 fragment in Δcts2 genome;

SEQ ID NO:25 depicts the nucleotide sequence of the reverse primer derived from the deleted fragment of CTS2, and used for PCR confirmation of deletion of CTS2 fragment in Δcts2 genome;

SEQ ID NO:26 depicts the nucleotide sequence of the digoxigenin-labeled probe, which was amplified by PCR from CTS2 gene, and used in southern analysis to confirm the homologous integration of pΔcts2 fragment at the CTS2 locus in the Δcts2 mutant;

SEQ ID NO:27 depicts the nucleotide sequence of the forward primer used for the PCR amplification of the probe of SEQ.ID-26;

SEQ ID NO:28 depicts the nucleotide sequence of the reverse primer used for the PCR amplification of the probe of SEQ.ID-26;

SEQ ID NO:29 depicts the nucleotide sequence of the forward primer derived from the BLE gene of pAN8-1, and used for PCR confirmation of integration of pΔcts3 in Δcts2Δard1Δcts3 genome;

SEQ ID NO:30 depicts the nucleotide sequence of the reverse primer derived from the BLE gene of pAN8-1, and used for PCR confirmation of integration of pΔcts3 in Δcts2Δard1Δcts3 genome;

SEQ ID NO:31 depicts the nucleotide sequence of the forward primer derived from the deleted fragment of ARD1/CTS3, and used for PCR confirmation of deletion of ARD1/CTS3 fragment in Δcts2Δard1Δcts3 genome;

SEQ ID NO:32 depicts the nucleotide sequence of the reverse primer derived from the deleted fragment of ARD1/CTS3, and used for PCR confirmation of deletion of ARD1/CTS3 fragment in Δcts2Δard1Δcts3 genome;

SEQ ID NO:33 depicts the nucleotide sequence of the digoxigenin-labeled probe, which was amplified by PCR from ARD1/CTS3 gene, and used in southern analysis to confirm the homologous integration of pΔcts3 fragment at the ARD1/CTS3 locus in the Δcts2Δard1Δcts3 mutant;

SEQ ID NO:34 depicts the nucleotide sequence of the forward primer used for the PCR amplification of the probe of SEQ.ID-33;

SEQ ID NO:35 depicts the nucleotide sequence of the reverse primer used for the PCR amplification of the probe of SEQ.ID-33;

SEQ ID NO:36 depicts the nucleotide sequence of URE gene; and

SEQ ID NO:37 depicts the derived amino acid sequence of the native Ure polypeptide encoded by the nucleotide sequence of SEQ ID NO:36.

DETAILED DESCRIPTION OF THE INVENTION

Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausubel et al (eds.), John Wiley & Sons, New York (2001) and the various references cited therein.

I. The Attenuated Fungi of the Invention.

Techniques to interfere with the regulatory mechanisms that control reproduction in the parasitic form of the *Coccidioides* spp. fungus are described herein. Methods have been devised that render the strains of the fungus incapable of producing endospores in the parasitic, spherule-endospore phase of the fungus. Such strains, while replication competent in the saprobic, mycelial phase, are incapable of causing disease in mammals because the loss of endosporulation potential results in their inability to propagate in the parasitic phase. Since the attenuated strains retain properties necessary for their immunogenicity, such strains would be useful for inducing a protective immune response, making them suitable as a preventative or therapeutic vaccine for coccidioidomycosis.

The general approach was to identify suitable sites for genetic alteration of the chromosome of the *Coccidioides* spp. fungus in order to create knockouts of genes, selecting those that regulate key stages of endosporulation and, therefore, render the recombinant fungus attenuated, while retaining properties of the strain necessary for its immunogenicity.

Suitable sites for integration of the targeting vector into the chromosome of the fungal strain are genes that in no way will effect properties of the strain necessary for its immunogenicity but will increase its safety when used as an immunizing composition. Such strains, while replication competent in the saprobic, mycelial phase, are incapable of causing disease in mammals because of their inability to propagate in the parasitic phase. Such attenuated strains would be useful for a preventative or therapeutic vaccine for coccidioidomycosis.

More specifically, using the methods and approaches described in Example 1 and those known in the art, for example, Sambrook et al., Molecular Cloning: A Laboratory Manual, Third Edition, Cold Spring Harbor Laboratory Press, New York (2001), Current Protocols in Molecular Biology, Ausubel et al (eds.), John Wiley & Sons, New York (2001) and the various references cited therein, attenuated mutant strains would be created by transformation of wild-type strain *Coccidioides* spp. with gene deletion plasmid vectors designed to delete, by double crossover events, polynucleotide sequences of genes essential for regulation of endosporulation in *Coccidioides* spp.

A group of genes for such knock-out strains includes but is not limited to those known to have differential expression in the different growth phases of *Coccidioides* spp.; for example genes encoding the proteins CTS1, CTS2, CTS3, CTS4, CTS5, CTS6, CTS7, CHS5, CHS7, BGL2, beta-glucosidase 3, beta-glucosidase 5, and parasitic phase-specific protein PSP-1. The genetic sequences encoding said proteins would be obtained as disclosed herein from a public database available at The Institute for Genomic Research (TIGR) web site at tigr.org using computational analyses of the partial genome database by application of the basic local alignment search tool (BLAST) (Altschul, S. F., T. L. Madden, A. A. Schäffer, J. Zhang, Z. Zhang, W. Miller, and D. J. Lipman. 1997. Gapped BLAST and PSI-BLAST: a new generation of protein database search programs. Nucleic Acids Research 25:3389-3402). Another group of genes for such knock-out strains includes but is not limited to the *Coccidioides* spp. orthologs of genes known to control cell wall development or morphogenesis in other fungi, for example genes encoding the following proteins: Psu1, a cell wall synthesis protein reported to be essential for cell wall synthesis in fission yeast (GenBank AB009980, Biochem Biophys Res Commun. 262(2): 368-741, 1999); verprolin (Vrp), involved in cytoskeletal organization and cellular growth in *Saccharomyces cerevisiae,* (GenBank Reflxp__324261.1, Mol Microbiol. 10(3):585-96, 1993); DigA, a protein in *Aspergillus nidulans* required for nuclear migration, mitochondrial morphology and polarized growth. (GenBank Reflnp_588498.1, Mol Genet Genomics. 266(4): 672-685, Epub 2001); FluG, a protein reportedly essential for asexual development of *Aspergillus nidulans* (GenBank AAC37414.1, Genetics, Vol. 158, 1027-1036, 2001); Ras2, a RAS related GTP-binding protein that controls morphogenesis, pheromone response, and pathogenicity in the plant fungal pathogen *Ustilago maydis* (GenBank AY149917, Eukaryotic Cell 1 (6): 954-966, 2002); HymA, a protein essential for the development of conidiophore in *Aspergillus nidulans* (GenBank AJ001157, Mol Gen Genet. 260(6):510-21, 1999). As used herein, ortholog means genes in different species that evolved from a common ancestral gene by speciation that retain the same or essentially the same function in the course of evolution. The known sequences from the non-*Coccidioides* fungi would be used to conduct BLAST searches of the *Coccidioides posadasii* sequence data available at the TIGR database in order to obtain the corresponding *Coccidioides* ortholog gene sequences.

The *Coccidioides* gene sequences would then be used to create sequence alignments using the translated nucleotide sequences of the contigs or complete gene sequences and the non-redundant protein database available from the National Center for Biotechnology Information (Wheeler, D. L., C. Chappey, A. E. Lash, D. D. Leipe, T. L. Madden, G. D. Schuler, T. A. Tatusova, and B. A. Rapp. 2000. Database resources of the National Center for Biotechnology Information. Nucleic Acids Research 28:10-14), BLASTX matches would be selected with Expect (E) values of $<10^{-4}$ as previously described (Kirkland, T. N., and G. T. Cole. 2002. Gene-finding in *Coccidioides immitis:* searching for immunogenic proteins, p. 247-254. In K. J. Shaw (ed.), Pathogen genomics: impact on human health. Humana Press, Totowa, N.J.). Once appropriate sequences are derived, using the methods described herein appropriate transforming plasmids would be constructed and the *Coccidioides* spp. wild-type strain would be transformed to selectively replace and or delete polynucleotide sequences of individual genes that encode the targeted polypeptides using plasmids designed to result in a double crossover event.

Using the methods described more fully in the Examples, the identity and homology of the mutant transformants would be confirmed by PCR, sequence analysis, and Southern blot analysis by the methods described herein and would be subsequently screened to confirm loss of morphogenic potential to the parasitic phase. Such strains would be further evaluated for confirmation of lack of virulence in the mouse model further described in the Examples. Strains demonstrating lack of virulence would be considered attenuated and would be subsequently screened to confirm their immunogenicity in the vaccination mouse model, further described in Example 3. If the vaccination experiment showed increased survival in mice vaccinated with the attenuated strain and challenged with the wild-type strain and a reduction in the recovery of viable fungus from the organs of necropsied mice, this would confirm the strain as an attenuated vaccine useful for prevention of coccidioidbmycosis.

A specific embodiment of the molecular strategy is a CTS2/ARD1/CTS3 knockout of the *Coccidioides* spp. fungus. The triple knockout of the CTS2, ARD1 and CTS3 genes of the *Coccidioides* spp. fungus was performed using targeted gene replacement in the wild-type gene sequences (SEQ ID NO:1, SEQ ID NO:9, and SEQ ID NO:7, respectively), resulting in homologous integration of a hygromycin resistance cassette and a phleomycin cassette by double crossover recombination at the flanking CTS2- and ARD1/CTS3-homologous fragments, respectively, and the consequent deletion of an internal fragment from both. The mutated CTS2 locus of the CTS2-null mutant would thus contain the transformation plasmid construct of SEQ ID NO:4, but lacks a fragment of CTS2 (SEQ ID NO:5) that intervenes the CTS2 sequences in homology to the flanks of the hygromycin cassette. Similarly, the mutated ARD1/CTS3 locus of the ARD1/CTS3-null mutant contains the transformation plasmid construct of SEQ ID NO:11, but lacks a fragment of ARD1/CTS3 (SEQ ID NO:12). The rest of the fungus DNA was left intact.

Although the strains described above include deletions of the ARD1 gene, it is anticipated that a double-knockout of the CTS2 and CTS3 genes, by the methods described herein, would result in mutant strains and vaccines functionally and immunologically equivalent to the strains of the present invention.

According to preferred embodiments, the fungus would maintain an ability to grow in vitro in the saprophytic, mycelial phase and could undergo morphogenic conversion into a first-generation parasitic-phase spherule when introduced into a mammal, but could not undergo endosporulation, thereby rendering it incapable of reproducing and, consequently, incapable of causing disease. The attenuated strain would, however, retain the potential to induce a protective immune response, thereby making it suitable for use as a preventative or therapeutic vaccine for prevention and or treatment of coccidioidomycosis. In additional embodiments, the introduction of additional deletions or sequence modifications that would reduce the virulence of the cts2/ard1/cts3-null mutant of *Coccidioides* spp. of the present invention or reduce the virulence of the cts2/ard1/cts3-null mutant in the event of reversion of the mutant strain to a wild-type phenotype, either through spontaneous reversion or recombination with a homologous or heterologous gene donor, would address a long-felt need in the art to provide attenuated vaccines for the prevention or treatment of coccidioidomycosis that have an increased margin of safety for use in a mammal.

II. The DNA Sequences of the Invention.

The methods utilized for selective replacement and or deletion of polynucleotide sequences in strains of *Coccidioides* spp. fungus, leading to the corresponding loss amino acids necessary for functional proteins critical to endosporulation potential of the parasitic phase of the fungus and, hence, virulence, are disclosed herein. Polynucleotide coding sequences for amino acid residues are known in the art and are disclosed for example in Molecular Cloning: A Laboratory Manual, Third Edition, Sambrook, Fritsch, and Maniatis, Cold Spring Harbor Laboratory Press, 2001.

As a representative example, using the methods disclosed herein, a *Coccidioides* spp. strain was created wherein the resulting transformed CTS2/ARD1/CTS3-null mutant had a recombinant CTS2 gene with 5667 nucleotide residues and a recombinant ARD1/CTS3 gene with 4849 nucleotide residues, which resulted in no detectable or functional CTS2- or CTS3-encoded polypeptides in transformants. The nucleotide sequence of the recombinant CTS2 gene of the present invention is the polynucleotide sequence-of SEQ ID NO:13, and the nucleotide sequence of the recombinant ARD1/CTS3 of the present invention is the polynucleotide sequence of SEQ ID NO:14.

By such methods, additional attenuated strains comprising the introduction of deletions or sequence modifications that would affect target polynucleotide sequences essential to endosporulation and or virulence of *Coccidioides* spp. are disclosed.

A further variation provides introduction of additional mutations in strains lacking endosporulation potential comprising deletion of sequences essential for the production of virulence factors other than those controlling endosporulation potential of *Coccidioides* spp. In one such embodiment, a null mutation of the URE gene is introduced into the cts2/ard1/cts3 null mutant strains, resulting in a functional disruption of the URE gene product.

Within the context of the present invention "polynucleotide" in general relates to polyribonucleotides and polydeoxyribonucleotides, it being possible for these to be non-modified RNA or DNA or modified RNA or DNA.

Polynucleotides of the present invention means the sequences exemplified in this application as well as those that have substantial identity to those sequences and which lead to loss of morphogenic potential of the *Coccidioides* spp. fungus. Preferably, such polynucleotides are those that hybridize under stringent conditions as defined herein and are at least 70%, preferably at least 80% and more preferably at least 90% to 95% identical to those sequences.

"Consisting essentially of", in relation to a nucleic acid sequence, is a term used hereinafter for the purposes of the specification and claims to refer to sequences of the present invention and sequences with substitution of nucleotides as related to third base degeneracy. As appreciated by those skilled in the art, because of third base degeneracy, almost every amino acid can be represented by more than one triplet codon in a coding nucleotide sequence. Further, minor base pair changes may result in variation (conservative substitution) in the putative amino acid sequence encoded, are not expected to substantially alter the attenuation or immunologic potential of the fungus. Thus, a nucleic acid sequence as disclosed herein, may be modified slightly in sequence (e.g., substitution of a nucleotide in a triplet codon), and yet still result in the loss of morphogenic conversion and virulence of the fungus because it consists essentially of the same sequence.

The terms "stringent conditions" or "stringent hybridization conditions" includes reference to conditions under which a polynucleotide will hybridize to its target sequence, to a detectably greater degree than other sequences (e.g., at least 2-fold over background). In particular, a DNA or polynucleotide molecule which hybridizes under stringent conditions is preferably at least 70%, 75%, 80%, 85%, 90%, 95%, 97%, 98% or 99% homologous to the DNA that encodes the amino acid sequences described herein. In a preferred embodiment these polynucleotides that hybridize under stringent conditions also encode a protein or peptide which upon administration to a subject provides an immunostimulation sufficient to provide some level of immune protection against *Coccidioides* spp. as described herein.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short polynucleotides (e.g., 10 to 50 nucleotides) and at least about 60° C. for long polynucleotides (e.g., greater than 50 nucleotides)—for example, "stringent conditions" can include hybridization in 50% formamide, 1 M NaCl, 1% SDS at 37° C., and three washes for 15 min each in 0.1× SSC/1% SDS at 60 to 65° C.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman (Advances in Applied Mathematics. 1981. 2: 482-489), to find the best segment of identity or similarity between two sequences. Gap performs global alignments: all of one sequence with all of another similar sequence using the method of Needleman and Wunsch, (Journal of Molecular Biology. 1970. 48:443-453). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Naturally, the present invention also encompasses DNA segments that are complementary, or essentially complementary, to the sequences set forth in SEQ ID NO:2 and or SEQ ID NO:7 [ORF sequences]. As used herein, the term "complementary sequences" means nucleic acid sequences that are substantially complementary, as may be assessed by the same nucleotide comparison set forth above, or as defined as being capable of hybridizing to the nucleic acid segments SEQ ID NO:2 and or SEQ ID NO:7 under stringent conditions such as those described herein.

The nucleic acid segments of the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that a nucleic acid segment or fragment of almost any length may be employed, with the total length preferably being limited by the ease of preparation and use in the intended recombinant protocol.

For example, nucleic acid segments or fragments may be prepared that include a short contiguous stretch identical to or complementary to SEQ ID NO:2 and or SEQ ID NO:7, such as about a 3,000, 5,000 or 10,000 bp nucleotide stretch, up to about 20,000 base pairs in length. Nucleic acid and DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 3001, 3002, 3003, 3004, 3005, etc.; including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,001, 20,001 and the like.

It will also be understood that this invention is not limited to the use of the particular plasmid sequences of SEQ ID NO:4 and SEQ ID NO:11 used for the transformation of the *Coccidioides* spp. fungus. Recombinant vectors and isolated DNA segments may therefore variously include the coding region from SEQ ID NO:4 or SEQ ID NO:11, coding regions bearing selected alterations or modifications in the basic coding region, or they may consist essentially of larger polynucleotide sequences that, when introduced into the *Coccidioides* spp. fungus, nevertheless result in the loss of genes that control endosporulation potential.

The nucleic acid and DNA segments of the present invention contain essentially equivalent polynucleotide sequences that arise as a consequence of point mutations that occur naturally or through the application of site-directed mutagenesis techniques or through such other techniques that are known to those skilled in the art.

III. Preparation and Formulation of Vaccines.

As described herein, the attenuated *Coccidioides* spp. strains may be introduced into a mammal by injection or other routes of instillation, in one or more administrations, thereby eliciting an immune response protective against *Coccidioides* spp. infection. In a further embodiment, the attenuated fungal strains and formulations employing the strains may be admixed in various combinations and or admixed with other known proteins or peptides which are known or believed to facilitate an immunological response, thereby providing protection against *Coccidioides* spp. infection. In an alternative embodiment, the components of the present invention may be administered separately; i.e., at different time points, which is known or believed to facilitate an immunological response, thereby providing protection against *Coccidioides* spp. infection. For example, the attenuated strain of the present invention can be combined with one or more additional *Coccidioides* spp. polypeptides or antigens, such as Ag2/PRA106, Csa, Gel1, Ure, or non-*Coccidioides* protein antigens or toxoids, such as tetanus toxoid, diphtheria toxoid, cholera toxoid, ovalbumin (OVA), or keyhole limpet haemocyanin (KLH).

The pharmaceutically acceptable carriers which can be used in the present invention include, but are not limited to, an excipient, a stabilizer, a binder, a lubricant, a colorant, a disintegrant, a buffer, an isotonic agent, a preservative, an anesthetic, and the like which are commonly used in a medical field.

Also, the dosage form, such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like, can be used appropriately depending on the administration method and the polypeptides of the present invention can be accordingly formulated. Pharmaceutical formulations are generally known in the art and are described, for example, in Chapter 25.2 of Comprehensive Medicinal Chemistry, Volume 5, Editor Hansch et al, Pergamon Press (1990).

The present invention also provides compositions containing the attenuated strains thereof and one or more suitable adjuvants commonly used in the field of immunology and medicine to enhance the immune response in a subject. Examples of such adjuvants include monophosphoryl lipid A (MPL), a detoxified derivative of the lipopolysaccharide (LPS) moiety of *Salmonella minnesota* R595, which has retained immunostimulatory activities and has been shown to promote Th1 responses when co-administered with antigens (see U.S. Pat. No. 4,877,611; Tomrai et al., Journal of Biological Response Modifiers. 1987. 6:99-107; Chen et al., Journal of Leukocyte Biology 1991. 49:416-422; Garg & Subbarao. Infection and Immunity. 1992. 60(6):2329-2336; Chase et al., Infection and Immunity. 1986. 53(3):711-712; Masihi et al, Journal of Biological Response Modifiers. 1988. 7:535-539; Fitzgerald, Vaccine 1991. 9:265-272; Bennett et al, Journal of Biological Response Modifiers 1988. 7:65-76; Kovach et al., Journal of Experimental Medicine, 1990. 172:77-84; Elliott et al., Journal of Immunology. 1991.10:69-74; Wheeler A. W., Marshall J. S., Ulrich J. T., International Archives of Allergy and Immunology 2001. October; 126(2):135-9; and Odean et al., Infection and Immunity 1990. 58(2):427-432); MPL derivatives (see U.S. Pat. No. 4,987,237) other general adjuvants (see U.S. Pat. No. 4,877,611); CpG and ISS oligodeoxynucleotides (see U.S. Pat. No. 6,194,388; U.S. Pat. No. 6,207,646; U.S. Pat. No. 6,239,116; U.S. Pat. No. 6,339,068; McCluskie, M. J., and H. L. Davis. Vaccine 2002. 19:413-422; Ronaghy A, Prakken B J, Takabayashi K, Firestein G S, Boyle D, Zvailfler N J, Roord S T, Albani S, Carson D A, Raz E. Immunostimulatory DNA sequences influence the course of adjuvant arthritis. Journal of Immunology 2002. 168(1):51-6.; Miconnet et al (2002) 168(3) Journal of Immunology pp 1212-1218; Li et al (2001) Vaccine 20(1-2):148-157; Davis (2000) Developmental Biology 104:165-169; Derek T. O'Hagan, Mary Lee MacKichan, Manmohan Singh, Recent developments in adjuvants for vaccines against infectious diseases, Biomolecular Engineering 18 (3) (2001) pp. 69-85; McCluskie et al (2001) Critical Reviews in Immunology 21(1-3):103-120); trehalose dimycolate (see U.S. Pat. No. 4,579,945); amphipathic and surface active agents, e.g., saponin and derivatives such as QS21 (see U.S. Pat. No. 5,583,112); oligonucleotides (Yamamoto et al, Japanese Journal of Cancer Research, 79:866-873, 1988); detoxified endotoxins (see U.S. Pat. No. 4,866,034); detoxified endotoxins combined with other adjuvants (see U.S. Pat. No. 4,435,386); combinations with QS-21 (see U.S. Pat. No. 6,146,632); combinations of detoxified endotoxins with trehalose dimycolate and endotoxic glycolipids (see U.S. Pat. No. 4,505,899); combinations of detoxified endotoxins with cell wall skeleton (CWS) or CWS and trehalose dimycolate (see U.S. Pat. Nos. 4,436,727, 4,436,728 and 4,505,900); combinations of just CWS and trehalose dimycolate, without detoxified endotoxins (as described in U.S. Pat. No. 4,520,019); chitosan adjuvants (see U.S. Pat. Nos. 5,912,000; 5,965,144; 5,980,912; Seferian, P. G., and Martinez, M. L. Immune stimulating activity of two new chitosan containing adjuvant formulations (2001) Vaccine. 2000. 19(6): 661-8). All of the references cited in this paragraph are incorporated herein by reference.

In another embodiment, various adjuvants, even those that are not commonly used in humans, may be employed in animals where, for example, one desires to subsequently obtain activated T cells or to protect valuable or valued animals from infection due to *Coccidioides* spp.

IV. Administration of Vaccines

As used herein the subject that would benefit from the administration of the attenuated vaccines and formulations described herein include any mammal that can benefit from protection against *Coccidioides* spp. infection. In a preferred embodiment, the subject is a human. In a second embodiment, the subject is a domestic animal, including but not limited to dog, cat, horse, bovine (meaning any sex or variety of cattle) or other such domestic animals.

By attenuated vaccine capable of eliciting an immune response in a subject human, including vaccination, the invention covers any strain of *Coccidioides* spp. incapable of endosporulation in the parasitic phase but that induces an immune reaction that results in or augments the subject's ability to mount some level of immune protection inhibiting *Coccidioides* spp. infection. In one embodiment, the *Coccidioides* spp. is *Coccidioides immitis*. In another embodiment, the *Coccidioides* spp. is *Coccidioides posadasii*.

As used herein, "inhibit", "inhibiting" or "inhibition" includes any measurable or reproducible reduction in the infectivity of *Coccidioides* spp. in the subject mammal. "Reduction in infectivity" means the ability of the subject to prevent or limit the spread of *Coccidioides* spp. fungus in tissues or organs exposed or infected by said fungus. Furthermore, "amelioration", "protection", "prevention" and "treatment" mean any measurable or reproducible reduction, prevention, or removal of any of the symptoms associated with *Coccidioides* spp. infectivity, and particularly, the prevention, or amelioration of *Coccidioides* spp. infection and resultant pathology itself.

The dosages used in the present invention to provide immunostimulation include from about 0.1 μg to about 2000 μg, which includes, 0.5, 1.0, 2.0, 5.0, 10, 20, 30, 40, 50, 60, 70, 80, 90, 100, 150, 200, 250, 300, 350, 400, 450, 500, 600, 800, 1000, 1500, and 1800 μg, inclusive of all ranges and subranges there between. Such amount may be administered as a single dosage or may be administered according to a regimen, including subsequent booster doses, whereby it is effective; e.g., the compositions of the present invention can be administered one time or serially over the course of a period of days, weeks, months and or years.

The compositions of the present invention can be administered by any suitable administration method including, but not limited to, injections (subcutaneous, intramuscular, intracutaneous, intravenous, intraperitoneal), oral administration, intranasal administration, inhalation, etc.

V. Kits.

Also included within the scope of the present invention are kits suitable for providing compositions of the attenuated *Coccicioides* spp. strains. For example, in such a kit one vial can comprise the attenuated fungus disclosed herein admixed with a pharmaceutically acceptable carrier, either in a aqueous, non-aqueous, or dry state; and a second vial which can carry immunostimulatory agents, and or a suitable diluent for the composition, which will provide the user with the appropriate concentration of fungus to be delivered to the subject. In one embodiment, the kit will contain instructions for using the composition and other components, as included; such instructions can be in the form of printed, electronic, visual, and or audio instructions. The vaccinations will normally be at from two to twelve week intervals, more usually from three to five week intervals. Periodic boosters at intervals of 1-5 years, usually three years, will be desirable to maintain protective levels. The course of the immunization may be followed by assays for activated T cells produced, skin-test reactivity, or other indicators of an immune response to *Coccidioides* spp.

Having generally described the attenuated strains of *Coccidioides* spp. useful as vaccines and the methods to create and administer them to elicit protective immune responses, a further understanding can be obtained by reference to certain specific examples that are provided herein for purposes of illustration only, and are not intended to be limiting unless otherwise specified.

EXAMPLES

Example 1

Creation and Characterization of CTS2/ARD1/CTS3 Null Mutant of *Coccidioides posadasii*

Material and Methods

Culture conditions. *C. posadasii* (isolate C735) was used for all experirmental procedures reported in this study. The saprobic (mycelial) phase of the fungus was grown on glucose-yeast extract agar (GYE; 1% glucose, 0.5% yeast extract, 2% agar) at 30° C. for 3 weeks for the production of arthroconidia, the asexual reproductive propagule of the saprobic phase, and mycelia, as required for subsequent procedures and experiments. Parasitic phase of the fungus was grown in defined glucose-salt medium supplemented with 20% $CO_2$ at 39° C. (Levine H. B. 1961. purification of the spherule-endospore phase of *Coccidioides immitis.* Sabouradia 1:112-115).

Genome database analysis and gene discovery. The *C. posadasii* genome sequencing project was initiated in 2001 at The Institute for Genomic Research (TIGR, Rockville, Md.), and involves a whole genome shotgun strategy for determination of >99% of the 29-megabase genome sequence. Genomic libraries of *C. posadasii* (isolate C735) with inserts of 2-10 kilobases (kb) were constructed in the pUC plasmid (Promega, Madison, Wis.), and sequenced from both ends. Each library contained $>6\times10^5$ recombinants, and the combined recombinants of three libraries have been estimated to be sufficient for sequence analysis of the entire *C. posadasii* genome (Kirkland, T. N., and G. T. Cole. 2002. Gene-finding in *Coccidioides immitis:* searching for immunogenic proteins, p. 247-254. In K. J. Shaw (ed.), Pathogen genomics: impact on human health. Humana Press, Totowa, N.J.). Genomic survey sequences (GSS) have been assembled into unique contigs and incorporated into a public database (available at The Institute for Genomic Research web site at tigr.org). Computational analyses of the partial genome database were performed by application of the basic local alignment search tool (BLAST) (Altschul, S. F., T. L. Madden, A. A. Schäffer, J. Zhang, Z. Zhang, W. Miller, and D. J. Lipman. 1997. Gapped BLAST and PSI-BLAST: a new generation of protein database search programs. Nucleic Acids Research 25:3389-3402). Sequence alignments were conducted using the translated nucleotide sequences of the contigs and the non-redundant protein database available from the National Center for Biotechnology Information (Wheeler, D. L., C. Chappey, A. E. Lash, D. D. Leipe, T. L. Madden, G. D. Schuler, T. A. Tatusova, and B. A. Rapp. 2000. Database resources of the National Center for Biotechnology Information. Nucleic Acids Research 28:10-14). BLASTX matches were selected with Expect (E) values of $<10^{-4}$ as previously described (Kirkland, T. N., and G. T. Cole. 2002.).

Construction of transformation plasmid. Two plasmids, pΔcts2 and pΔcts3, were constructed to disrupt CpCTS2 and ARD1/CTS3 genes, respectively, by homologous recombination. To construct the pΔcts2 plasmid, one pair of synthetic oligonucleotide primer (SEQ ID NO:15 and SEQ ID NO:16) was used to amplify the CpCTS2 gene from genomic DNA of *Coccidioides posadasii* C735 strain. The 3041-bp PCR product (SEQ ID NO:1 nt 1-3041) was then cloned into a PCR2.1-TOPO vector (Invitrogen™ Life Technologies, Inc., San Diego, Calif.) to yield the pCR2.1-CTS2 plasmid. The pΔcts2 plasmid was obtained by replacing a 1-kb STuI/SpeI CTS2 fragment (SEQ ID NO:1 nt 829-1795) in the pCR2.1-CTS2 plasmid with a 3.6-kb STuI/XbaI fragment of pAN7-1 (GenBank accession # Z32698) by standard molecular cloning method (Sambrook, J., Fritsch, E. F, & Maniatis T. 1989. Molecular cloning: a laboratory manual, $2^{nd}$ ed. Cold Spring Harbor Laboratory Press, Cold Spring Harbor, N.Y.). The 3.6-kb pAN7-1 polynucleotide contains the hygromycin B phosphotransferase gene (HPH) (Punt, P J., Oliver, R P., Dingemanse, M A., Pouwels, P H., and van den Hondel, C A. 1987. Transformation of *Aspergillus* based on the hygromycin B resistance marker from *Escherichia coli.* Gene 56:117-124), which confers resistance to the transformation selection marker, hygromycin. The pΔcts2 plasmid was used to transform an *E. coli* strain TAM-1 (Activemotif, Carlsbad, Calif.). The pΔcts2 plasmid was isolated from the transformed bacteria, linearized by digestion with ApaI and DraI at the pCR2.1-TOPO vector, extracted by ethanol precipitation, suspended in MSC buffer (10 mM MOPS, pH 6.5; 1 M sorbitol and 20 mM $CaCl_2$) and held for transformation. The 6891-bp ApaI/DraI fragment (SEQ ID NO:4) of pΔcts2, includes the 3597-bp pAN7-1 fragment, 828- and 1242-bp flanks of CpCTS2-homologous fragments, and 63- and 1161-bp fragments of pCR2.1-TOPO.

To construct the pΔcts3 plasmid, one pair of synthetic oligonucleotide primer (SEQ ID NO:17 and SEQ ID NO:18) was used to amplify the ARD1/CTS3 gene from genomic DNA of *Coccidioides posadasii* C735 strain. The 2936-bp PCR product (SEQ ID NO:6 nt 1-2936) was then cloned into a PCR2.1-TOPO vector (Invitrogen™) to yield the pCR2.1-CTS3 plasmid. The pΔcts3 plasmid was obtained by replacing a 1.2-kb NheI/SspI ARD1/CTS3 fragment (SEQ ID NO:6 nt 972-2195) in the pCR2.1-CTS3 plasmid with a 3.1-kb NheI/SspI fragment of pAN8-1 (GenBank accession # Z32751) by standard molecular cloning method. The 3.1-kb pAN8-1 polynucleotide contains the phleomycin binding protein gene (BLE) (Punt et al. 1988. A vector for Aspergillus transformation conferring phleomycin resistance. Journal Fungal Genetics Newsletter 35:25-30), which confers resistance to the transformation selection marker, phleomycin. The pΔcts3 plasmid was used to transform an *E. coli* strain TAM-1 (Activemotif, Carlsbad, Calif.). The pΔcts3 plasmid was isolated from the transformed bacteria, linearized by digestion with ApaI and KpnI at the pCR2.1-TOPO fragment, extracted by ethanol precipitation, suspended in MSC buffer and held for transformation. The 4967-bp ApaI/KpnI fragment (SEQ ID NO:11) of pΔcts3, includes the 3137-bp pAN8-1 fragment, 971- and 741-bp flanks of ARD1/CTS3-homologous fragments, and 63- and 55-bp fragments of pCR2.1-TOPO.

Fungal transformation procedures. Transformation of *Coccidioides posadasii* was performed using a reported method (Reichard et al. 2000. Disruption of the gene, which encodes a serodiagnostic antigen and chitinase of the human fungal pathogen *Coccidioides immitis*. Infection and immunity 68:5830-8). The 7-kb ApaI/DraI fragment of pΔcts2, was taken up by the protoplasts of *C. posadasii* C735 in the presence of polyethylene glycol and calcium ion. Transformants were selected on GYE agar supplemented with 75 μg/ml hygromycin B (HmB) and subsequently maintained on 100 μg/ml HmB/GYE agar. A Δcts2 mutant (#63) confirmed by Southern blot analysis was used as the parental strain for second transformation to disrupt ARD1/CTS3 genes. Transformation of Δcts2 mutant with the 5-kb ApaI/KpnI fragment of the pΔcts3 plasmid was performed as described above except transformants were selected on GYE agar supplemented with 3 μg/ml phleomycin (PHL) and subsequently maintained on 5 μg/ml PHL/GYE agar.

Screening of putative transformants. Total genomic DNA was extracted with CTAB (hexadecyltrimethylammonium bromide) buffer (2% w/v CTAB, Sigma; 100 mM Tris-HCl, pH 8.0; 1.4 M NaCl; 20 mM EDTA, pH 8.0; 0.2% v/v β-mercaptoethanol) in 1.5-ml microtubes. About 1 $cm^2$ of mycelia from 10-days-old cultures in GYE agar and 500 μL of sterile, acid-washed glass beads (425-600 μM; Sigma) were suspended in 500 μL of CTAB buffer, and the cells were disrupted at high speed (500 rpm for 30 s) in a bead beater. Genomic DNA was extracted twice with 500 μL of chloroform/isoamyl alcohol and precipitated with two volumes of cold ethanol following the standard protocol (Sambrook, J., Fritsch, E. F, & Maniatis T. (1989). Molecular cloning: a laboratory manual, 2nd ed. Cold Spring Harbor Laboratory Press, Cold Spring Harbor, N.Y.). The identity of transformants as *C. posadasii* was confirmed by PCR using primers SEQ ID NO:20 and SEQ ID NO:21 derived from the gene encoding a *Coccidioides*-specific antigen (CSA; [SEQ ID NO:19]) (Pan S, Cole G T. 1995. Molecular and biochemical characterization of a *Coccidioides immitis*-specific antigen. Infection and Immunity 63: 3994-4002). To identify Δcts2 mutants, PCR was used to screen hygromycin-resistance transformants for presence of HPH gene with a pair of HPH-specific primer (SEQ ID NO:22 and SEQ ID NO:23) and absence of the deleted CTS2 gene sequence with a primer pair (SEQ ID NO:24 and SEQ ID NO:25) derived from the deleted region of CTS2. Southern blot analysis was used to further confirm targeted disruption of CTS2 in the putative transformants. Genomic DNA isolated from selected pΔcts2 transformants were digested with XhoI, Sa/I or HindIII, separated in agarose gel by electrophoresis, transferred to nitrocellulose membrane, and hybridized with HPH- or CTS2-specific probe using standard protocols (Sambrook, J., Fritsch, E. F, & Maniatis T. 1989. Molecular cloning: a laboratory manual, 2nd ed. Cold Spring Harbor Laboratory Press, Cold Spring Harbor, N.Y.). Probes were derived by PCR amplification using the HPH-specific primer pair (SEQ ID NO:22 and SEQ ID NO:23) or CTS2-specific primer pair (SEQ ID NO:27 and SEQ ID NO:28). The PCR-derived probes were conjugated with digoxigenin-11-dUTP (Boehringer, Mannheim, Germany) during the amplification reaction, and digoxigenin was detected with specific peroxidase-labeled antibody as recommended by the supplier.

To identify ⊿cts2⊿ard1⊿cts3 mutants, PCR was used to screen phleomycin-resistance transformants for presence of BLE gene with a pair of BLE-specific primer (SEQ ID NO:29 and SEQ ID NO:30) and absence of the deleted ARD1/CTS3 gene sequence with a primer pair (SEQ ID NO:31 and SEQ ID NO:32) derived from the deleted region of ARD1/CTS3. Southern blot analysis was used to confirm targeted disruption of ARD1/CTS3 with homologous recombination in the positive PCR colonies. BLE-specific probe was used to hybridize Mu/I- and NcoI-restricted genomic DNA isolated from selected pΔcts3 transformants, and ARD1/CTS3-specific probe was used to probe NcoI and HindIII+XmaI digests of genomic DNA from the same p⊿cts3 transformants in the Southern analyses as described above. Probes were derived by PCR amplification using the BLE-specific primer pair (SEQ ID NO:29 and SEQ ID NO:30) or ARD1/CTS3-specific primer pair (SEQ ID NO:34 and SEQ ID NO:35).

Results

Generation of Δcts2 mutants. The linearized fragment of the plasmid construct, pΔcts2, was designed to integrate into *C. posadasii* chromosomal DNA by a double crossover event at the CpCTS2 locus. Transformation of *C. posadasii* protoplasts with pΔcts2 yielded more than one hundred hygromycin-resistant colonies. A total of 19 transformants were identified as HPH-positive and CTS2-negative colonies by PCR using specific primers. Six of these transformants were subjected to Southern blot analysis, and four ⊿cts2 mutants with homologous recombination by double crossover were identified. The CTS2 probe hybridized with a 4.3-kb XhoI, a 8.3-kb Sa/I, and a 10-kb HindIII DNA digests of ⊿cts2 mutants, as well as a 6-kb XhoI, a 8.2 Sa/I, and a 7.5-kb HindIII digests of wild type. The HPH probe only detected a single band from each restriction digests of ⊿cts2 mutants (4.3-kb XhoI, 8.3-kb Sa/I, 10-kb HindIII) but not the DNA digests of wild type. Sizes of hybridization bands were all agreed to restriction maps of CTS2 gene and of hypothetical sequences with pΔcts2 integrated into the CTS2 locus. One well characterized ⊿cts2 mutant, #63, was used for second transformation to knock out CTS3 gene.

Generation of a ⊿cts2⊿ard1⊿cts3 mutant. A plasmid (pΔcts3) was constructed to generate a ⊿cts2⊿cts3 double mutant; however an ARD1 gene was simultaneously deleted with the downstream CTS3 gene. The genome is very compact at the CTS3 locus, only 697-bp apart between the end of ARD1 stop codon and the beginning of CTS3 start codon. When pΔcts3 was constructed, half of the ARD1 open reading frame (ORF; SEQ ID NO:9 nt 473-813; SEQ ID NO:10 aa 158-270) was deleted along with part of the ORF of CTS3 (SEQ ID NO:7 nt. 1-186; SEQ ID NO:8 aa 1-62). The terminator of ARD1 gene and promoter of CTS3 were also deleted. Only one phleomycin-resistance. transformant (#DG71) was identified as BLE-positive and ARD1/CTS3-negative colonies by PCR using specific primers. Southern blot analysis confirmed this transformant has deletion at the ARD1/CTS3 loci resulted by double crossover with the introduced pΔcts3 DNA. The ARD1/CTS3 probe hybridized with a 4.2-kb NcoI and a 4.6-kb HindIII+XmaI DNA digests of the Δcts2Δard1Δcts3 mutant, as well as a 2.9-kb NcoI and a 3.3-kb HindIII+XmaI digests of both wild type and Δcts2(#63). The BLE probe only detected a single band from each restriction digests of the ⊿cts2⊿ard1⊿cts3 mutant (2.4-kb NcoI, 4.7-kb Mu/I) but not the DNA digests of wild type or ⊿cts2(#63). Sizes of all hybridization bands were agreed to restriction maps of ARD1/CTS3 gene and of hypothetical sequences with pΔcts3 integrated into the ARD1/CTS3 loci. Southern blot analyses of restriction digests of ⊿cts2 and ⊿cts2⊿ard1⊿cts3 DNA with CTS2-specific probe revealed identical hybridization patterns (4.3-kb XhoI, 10-kb HindIII) between these two mutants. Summary of all the Southern data indicates a ⊿cts2⊿ard1⊿cts3 triple mutant of *Coccidioides posadasii* was generated by targeted disruption of these three genes.

Morphology of the Δcts2Δard1Δcts3 Mutant.

The ⊿cts2⊿ard1⊿cts3 mutant strain of the present invention grows as a typical wild-type colony, when cultured on GYE agar. Microscopic examination revealed normal saprobic phase growth, with production of viable arthroconidia. However, the first-generation spherules produced in vitro in Converse media were unable to endosporulate, typically formed in chains, and gave rise to hyphal elements. When the ⊿cts2⊿ard1⊿cts3 mutant strain was introduced into mice, sterile spherules were also produced in vivo, and germinated to produce short hyphal elements.

Example 2

Evaluation of Virulence of CTS2/ARD1/CTS3-Null Mutant (Δcts2Δard1Δcts3) in BALB/c Mice.

Materials and Methods

The virulence of the mutant was assessed in female BALB/c mice at ages 7-8 weeks by the following method. Arthroconidia of the ⊿cts2⊿ard1⊿cts3 strain of the present invention and the wild type *C. posadasii* were used for infection of mice. Fungi were grown on glucose-yeast extract agar (GYE; 1% glucose, 0.5% yeast extract, 2% agar) at 30° C. for 3 weeks. The arthroconidia were then suspended in 10 ml of PBS. The number of arthroconidia in the suspension was counted with a hemocytometer, and the colony forming units (CFU) determined by agar plating.

PBS suspensions (200 CFU) of the wild type and Δcts2Δard1Δcts3 mutant strains were administered intranasally (i.n.) separately in either of two groups of ten BALB/c mice. Mice were scored for survival over a 40-day period post-challenge. Survivors were sacrificed at day 41 post-challenge to determine the residual CFU in the lungs and spleen.

Results

In the survival test, there was 100% survival of the mice injected with Δcts2Δard1Δcts3 by 40 days post-challenge, while none of the mice injected with the wild-type parental strain of *C. posadasii* survived beyond 21 days. There were no detectable (<10) fungal cells in either the lungs or spleen of all the surviving mice using fungal burden assays. The results confirm that the ⊿cts2⊿ard1⊿cts3 mutant strain had been attenuated by the complete loss of virulence, compared to wild-type *C. posadasii.*

Example 3

Evaluation of Δcts2Δard1Δcts3 Mutant Strain as a Vaccine Against *Coccidioides posadasii* Infection in BALB/c Mice.

Materials and Methods

Preparation of vaccines. Fungal suspensions, used in the vaccine to be tested, were produced from 3-week-old cultures of the ⊿cts2⊿ard1⊿cts3 mutant strain grown on GYE agar. Arthroconidia were suspended in PBS and passed over a nylon wool fiber column (Polysciences, Inc. Warrington, Pa.) to remove hyphal elements. The filtered arthroconidia were washed three times with PBS, resuspended in PBS, and the cells were enumerated by hemocytometer counts., Viability was assessed by plating appropriate dilutions on GYE agar, and the CFU determined. The negative control preparation was phosphate buffered saline (PBS).

Vaccination groups and challenge protocol. Groups of mice, each comprising 8-week-old female BALB/c mice, were used in this study. Duplicate groups of mice were vaccinated twice (two week interval), first with 50,000 arthroconidia followed by a second boosting vaccination of 25,000 arthroconidia of the ⊿cts2⊿ard1⊿cts3 mutant strain vaccine delivered subcutaneously in 100 μL. Duplicate groups of mice also received the PBS negative control. Four weeks after the second immunization, each mouse was infected by the intranasal route with 76 viable arthroconidia of wild-type *C. posadasii* in a volume of 30 μL (Lawrence R M, Huston A C, & Hoeprich P D. 1977. Reproducible method for induction pulmonary coccidioidomycosis in mice. Journal of Infectious Diseases 135:117-119.). Intranasal administration of arthroconidia was done under light halothane (1,1,1-trifluoro-2,2-chlorobromoethane) anesthesia. One of the paired groups of infected mice (⊿cts2⊿ard1⊿cts3 mutant strain vaccine or PBS) were monitored for survival for 75 days. The other groups of vaccinated or PBS injected mice were held for 15 days after infection and then were necropsied for determination of the extent of lung infection by plating of homogenized lung on GYE agar and quantitation of residual wild-type fungal colony forming units (CFU).

Results

In the survival experiment, as a result of challenge, 100% of mice from the PBS negative control group died within 17 days after challenge with *C. posadasii.* In marked contrast, there was complete protection of mice vaccinated with the ⊿cts2⊿ard1⊿cts3 mutant strain vaccine, with all mice surviving at the end of the 75 day observation period.

As additional evidence of protection conferred by the ⊿cts2⊿ard1⊿cts3 mutant strain vaccine, mice were necropsied 15 days after challenge for the quantitation of fungal burden in the lungs of the mice. The results showed that while the PBS control animals were heavily infected, with a geometric mean of $Log_{10}$CFU/organ equal to 7.36±1.12, the mice vaccinated with the Δcts2Δard1Δcts3 mutant strain vaccine had only 1.43±0.93, a statistically significant difference (P<0.001). These results confirm the utility of the attenuated Δcts2Δard1Δcts3 mutant strain as a vaccine for the prevention of coccidioidomycosis, as evidenced by the complete protection of the vaccinated mice challenged by an otherwise highly lethal challenge.

The following experiments are proposed as an additional example that could be conducted to further illustrate the utility of the invention:

Example 4

Evaluation of Δcts2Δard1Δcts3Δure Mutant Strain as a Vaccine Against *Coccidioides posadasii* Infection in BALB/c Mice.

Materials and Methods

Using the general methods and approaches described in Example 1 and those known in the art, for example, Sambrook et al., Molecular Cloning: A Laboratory Manual, Third Edition, Cold Spring Harbor Laboratory Press, New York (2001), Current Protocols in Molecular Biology, Ausubel et al (eds.), John Wiley & Sons, New York (2001) and the various references cited therein, attenuated mutant strains would be created by transformation of the Δcts2Δard1Δcts3 mutant strain with gene deletion plasmid vectors designed to delete polynucleotide sequences of the URE gene essential for encoding functional URE protein. For instance, one can generate a URE-disruption plasmid (pΔure) which contains a 800-bp 5' URE gene fragment amplified by PCR (SEQ ID NO:36 nt 1-800) followed by a 848-bp 3' URE gene fragment also generated by PCR (SEQ ID NO:36 nt 4741-5588). The Δcts2Δard1Δcts3 mutant can be transformed by the introduced pΔure using the transformation procedure described in example 1. Putative Δcts2Δard1Δcts3Δure mutants would be incapable of producing the functional Ure protein of SEQ ID NO:37, and such mutants can be selected on Difco Bacto Urea agar base medium containing a phenol red pH indicator. Transformants with disrupted URE gene would fail to change the color of medium from yellow to red. The identity of the Δcts2Δard1Δcts3Δure mutant can be further confirmed by PCR, sequence analysis, and Southern blot analysis by the methods described herein. The Δcts2Δard1Δcts3Δure strains would be evaluated for confirmation of lack of virulence in the mouse model previously described (Example 2). The Δcts2Δard1Δcts3Δure would be subsequently screened to confirm their immunogenicity in the vaccination mouse model by the methods described below.

Preparation of vaccines. Fungal suspensions, used in the vaccines to be tested, would be produced from 3-week-old cultures of the Δcts2Δard1Δcts3Δure mutant strain grown on GYE agar. Arthroconidia from the strains would be suspended in PBS and passed over a nylon wool fiber column (Polysciences, Inc. Warrington, Pa.) to remove hyphal elements. The filtered arthroconidia would be washed three times with PBS, resuspended in PBS, and the cells enumerated by hemacytometer counts., Viability would be assessed by plating appropriate dilutions on GYE agar, and the CFU determined. The negative control preparation would be PBS.

Vaccination groups and challenge protocol. Groups of mice, each comprising 8-week-old female BALB/c mice, would be used in the study. Groups of mice would be vaccinated either once or twice with 25,000-50,000 arthroconidia of the Δcts2Δard1Δcts3 mutant strain vaccine delivered subcutaneously in 100 μL or the PBS control. Four weeks after the second immunization, each mouse would be infected by the intranasal route with a highly lethal challenge of 75-100 viable arthroconidia of wild-type *C. posadasii* in a volume of 30 μL (Lawrence R M, Huston A C, & Hoeprich P D. 1977. Reproducible method for induction pulmonary coccidioidomycosis in mice. Journal of Infectious Diseases 135:117-119). Infected mice would be monitored for survival for 45-75 days.

Results

In mice successfully immunized by vaccination, protection would be conferred in mice against *C. posadasii* infection. This would be demonstrated by a significant difference between the survival of Δcts2Δard1Δcts3Δure mutant strain-vaccinated mice and negative control mice after the intranasal challenge with wild-type *C. posadasii.* For example, all Δcts2Δard1Δcts3Δure mutant strain-vaccinated mice would be expected to survive beyond the 45-75 day period of observation, while all the control animals would be dead by 15-25 days after challenge. At the end of the experiment, the surviving mice would be necropsied and examined. Evidence of localized nodules of healed abscesses would be expected in the lungs of the Δcts2Δard1Δcts3Δure mutant strain-vaccinated mice. Cultures of lung homogenates of the surviving mice would be expected to have reduced or no detectable CFU, indicating that they had acquired significant immunity to the otherwise lethal infection.

These results would confirm the utility of the attenuated Δcts2Δard1Δcts3Δure mutant strain to induce a protective immune response and to serve as a useful vaccine for the prevention of coccidioidomycosis, as evidenced by the complete protection of the vaccinated mice challenged by an otherwise highly lethal challenge.

What is claimed is:

1. A *Coccidioides posadasii* fungus comprising a polynucleotide with the sequence of SEQ ID NO:13 and a polynucleotide with the sequence of SEQ ID NO:14.

2. A composition comprising the fungus of claim 1 in combination with a pharmaceutically acceptable carrier.

3. A live, attenuated *Coccidioides posadasii* vaccine comprising the fungus of claim 1.

4. A method of eliciting an immune response in a mammal comprising the step of administering to the mammal a composition comprising the fungus of claim 1 in an amount sufficient to elicit an immune response.

5. The method of claim 4, wherein said mammal is a human.

6. The method of claim 4, wherein said mammal is a domestic animal selected from the group consisting of dog, cat, horse, and bovine.

7. The method of claim 4, wherein the recombinant fungus is administered to the mammal by subcutaneous injection or by intramuscular injection.

* * * * *